US006897059B2

(12) United States Patent
Foltz et al.

(10) Patent No.: US 6,897,059 B2
(45) Date of Patent: May 24, 2005

(54) STERILIZATION INDICATOR WITH CHEMICALLY STABILIZED ENZYME

(75) Inventors: William E. Foltz, Cottage Grove, MN (US); Robert A. Asmus, Hudson, WI (US); Ronald G. Lulich, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 338 days.

(21) Appl. No.: 10/014,736

(22) Filed: Dec. 11, 2001

(65) Prior Publication Data
US 2003/0162243 A1 Aug. 28, 2003

Related U.S. Application Data

(60) Division of application No. 09/228,712, filed on Jan. 12, 1999, now Pat. No. 6,355,448, which is a continuation-in-part of application No. 09/088,859, filed on Jun. 2, 1998, now abandoned.

(51) Int. Cl.⁷ .............................................. C12M 1/34
(52) U.S. Cl. ................... 435/287.6; 435/31; 435/288.5
(58) Field of Search .......................... 435/287.6, 288.1, 435/288.5, 31, 188, 29, 32, 34, 177, 178, 180, 287.4, 288.2, 288.4, 288.7

(56) References Cited

U.S. PATENT DOCUMENTS

| 3,239,429 A | 3/1966 | Menolasino et al. .......... 195/54 |
| 3,440,144 A | 4/1969 | Andersen ................. 195/103.5 |
| 3,661,717 A | 5/1972 | Nelson ..................... 195/103.5 |
| 4,115,068 A | 9/1978 | Josyln ......................... 422/56 |
| 4,145,186 A | 3/1979 | Andersen ...................... 23/232 |
| 4,240,926 A | 12/1980 | McNeely ................... 252/408 |
| 4,304,869 A | 12/1981 | Dyke ......................... 435/296 |
| 4,580,682 A | 4/1986 | Gorski et al. ............... 206/569 |
| 4,594,223 A | 6/1986 | Dyke et al. .................. 422/56 |
| 4,596,696 A | 6/1986 | Scoville, Jr. ................. 422/61 |
| 4,636,472 A | 1/1987 | Bruso ........................ 435/287 |
| 4,642,165 A | 2/1987 | Bier .......................... 203/12 |
| 4,643,876 A | 2/1987 | Jacobs et al. ................ 422/23 |
| 4,650,479 A | 3/1987 | Insley ........................ 604/358 |
| 4,692,307 A | 9/1987 | Bruso ......................... 422/58 |
| 4,699,765 A | 10/1987 | Hambleton .................. 422/57 |
| 4,739,881 A | 4/1988 | Bruso ........................ 206/305 |
| 4,756,882 A | 7/1988 | Jacobs et al. ................ 422/23 |
| 4,797,255 A | 1/1989 | Hatanaka et al. ............. 422/28 |
| 4,828,797 A | 5/1989 | Zwarun et al. ............... 422/55 |
| 4,839,291 A | 6/1989 | Welsh et al. ................ 435/296 |
| 4,863,688 A | 9/1989 | Schmidt et al. .............. 422/28 |
| 4,883,641 A | * 11/1989 | Wicks et al. ................. 422/50 |
| 4,914,034 A | 4/1990 | Welsh et al. |
| 315,600 A | 3/1991 | Niven |
| 5,057,433 A | 10/1991 | Douglas |
| 5,064,576 A | 11/1991 | Suto |
| 5,073,488 A | * 12/1991 | Matner et al. ................ 435/31 |
| 5,084,239 A | 1/1992 | Moulton et al. .............. 422/22 |
| 5,115,166 A | 5/1992 | Campbell ................. 315/111.21 |
| 5,178,829 A | 1/1993 | Moulton et al. .............. 422/23 |
| 5,184,046 A | 2/1993 | Campbell ................. 315/111.21 |
| 5,217,901 A | 6/1993 | Dyckman ................... 435/291 |
| 5,223,401 A | * 6/1993 | Foltz et al. ................... 435/18 |
| 5,252,484 A | * 10/1993 | Matner et al. ............ 435/287.4 |
| 5,270,217 A | 12/1993 | Dyke |
| 5,389,336 A | 2/1995 | Childers ...................... 422/28 |
| 5,405,580 A | 4/1995 | Palmer ........................ 422/28 |
| 5,418,167 A | * 5/1995 | Matner et al. ............ 435/287.4 |
| 5,478,749 A | 12/1995 | Dyke |
| 5,482,684 A | 1/1996 | Martens et al. ............. 422/119 |
| 5,486,459 A | 1/1996 | Burnham et al. ............. 435/31 |
| 5,500,184 A | 3/1996 | Palmer ......................... 422/2 |
| 5,516,648 A | 5/1996 | Malchesky et al. ........... 435/31 |
| 5,552,320 A | 9/1996 | Smith ...................... 435/287.4 |
| 5,620,656 A | 4/1997 | Wensky et al. |
| 5,667,753 A | 9/1997 | Jacobs et al. ................. 422/29 |
| 5,674,450 A | 10/1997 | Lin et al. ...................... 422/29 |
| 5,739,004 A | 4/1998 | Woodson ..................... 435/31 |
| 5,750,184 A | * 5/1998 | Imburgia ................... 427/2.13 |
| 5,770,393 A | 6/1998 | Dalmasso et al. ............ 422/31 |
| 5,785,934 A | 7/1998 | Jacobs et al. ................ 427/29 |
| 5,788,941 A | 8/1998 | Dalmasso et al. ............ 422/33 |
| 5,795,730 A | 8/1998 | Tautvydas ................... 435/31 |
| 5,801,010 A | 9/1998 | Falkowski et al. ............ 435/31 |

(Continued)

FOREIGN PATENT DOCUMENTS

| AU | 676743 | 12/1994 |
| EP | 0 254 428 A | 1/1988 |
| EP | 0 255 229 A2 | 2/1988 |

(Continued)

OTHER PUBLICATIONS

Alfa et al., "Comparison of Ion Plasma, Vaporized Hydrogen Peroxide, and 100% Ethylene Oxide Sterilizers to the 12/88 Ethylene Oxide Gas Sterilizer", *Infection Control and Hospital Epidemiology*, vol. 17, No. 2, Feb. 1996, pp. 92–100.

Baker, et al., "Thermal Stabilization of Fungal β–Glucosidase through Glutaraldehyde Crosslinking," *Biotechnology Letters*, vol. 10, No. 5, 325–330 (1988).

Barbaric, et al., "Stabilization of Glycoenzymes by Cross–linking of Their Carbohydrate Chains," *Annals New York Academy of Sciences*, vol. 542, pp. 173–179 (1988).

(Continued)

Primary Examiner—Ralph Gitomer
(74) Attorney, Agent, or Firm—Daniel R. Pastirik

(57) ABSTRACT

A sterilization indicator for testing the effectiveness of a sterilization procedure comprises a source of an enzyme, a sterilant-resistant chemical associated with the enzyme, and a substrate that reacts with the enzyme to form a detectable enzyme-modified product that provides an indication of the failure of the sterilization procedure. The sterilant-resistant chemical may be a polyglycerol alkyl ester, polyglycerol alkyl ether, an ethoxylated polyhydric alcohol ester, or a polyhydric alcohol ether. The indicator may be used to test the effectiveness of a hydrogen peroxide plasma sterilization procedure and may be provided with a non-challenge test pack or a lumen-challenge test pack.

11 Claims, 5 Drawing Sheets

U.S. PATENT DOCUMENTS

| | | | |
|---|---|---|---|
| 5,830,683 A | 11/1998 | Hendricks et al. | 435/31 |
| 5,856,118 A | 1/1999 | Dalmasso | 435/31 |
| 5,866,356 A * | 2/1999 | Albert et al. | 435/31 |
| 5,872,004 A | 2/1999 | Bolsen | |
| 5,895,627 A | 4/1999 | Khachatoorian | |
| 5,916,816 A | 6/1999 | Read | |
| 5,942,438 A | 8/1999 | Antonoplos et al. | |
| 6,063,631 A | 5/2000 | Ignacio | |
| 6,105,761 A | 8/2000 | Peuker et al. | |
| 6,287,518 B1 | 9/2001 | Ignacio et al. | |
| 6,346,417 B1 | 2/2002 | Ignacio et al. | |
| 6,355,448 B1 * | 3/2002 | Foltz et al. | 435/31 |
| 6,485,971 B1 | 11/2002 | Kaur et al. | |
| 6,485,978 B1 | 11/2002 | Kirckof et al. | |
| 6,485,979 B1 | 11/2002 | Kippenhan et al. | |
| 6,488,890 B1 | 12/2002 | Kirckof | |
| 6,566,090 B2 * | 5/2003 | Witcher et al. | 435/31 |
| 6,623,955 B2 * | 9/2003 | Matner et al. | 435/287.4 |
| 2002/0037546 A1 | 3/2002 | Hendricks et al. | |
| 2002/0051733 A1 | 5/2002 | Antonoplos et al | |
| 2002/0058296 A1 | 5/2002 | Miller et al. | |
| 2003/0077688 A1 * | 4/2003 | Matner et al. | 435/31 |
| 2003/0157588 A1 * | 8/2003 | Matner et al. | 435/31 |
| 2003/0215923 A1 * | 11/2003 | Witcher et al. | 435/71.1 |

FOREIGN PATENT DOCUMENTS

| | | |
|---|---|---|
| EP | 0 419 282 B1 | 3/1991 |
| EP | 0 421 760 A1 | 4/1991 |
| EP | 0 421 760 B1 | 3/1994 |
| EP | 0 638 650 A1 | 2/1995 |
| EP | 0 707 186 A1 | 4/1996 |
| JP | 62/115266 | 5/1987 |
| JP | 62/205748 | 9/1987 |
| JP | 62/205750 | 9/1987 |
| JP | 62/253357 | 11/1987 |
| JP | 63/079579 | 4/1988 |
| JP | 63/275517 | 11/1988 |
| WO | WO 94/28164 | 12/1994 |
| WO | WO 97/26924 | 7/1997 |
| WO | WO 98/46994 | 10/1998 |
| WO | WO 01/10473 A1 | 2/2001 |
| WO | WO 01/40792 A1 | 6/2001 |

OTHER PUBLICATIONS

Corry, J., "The Effect of Sugars and Polyols on the Heat Resistance of Salmonellae," *J. Appl. Bact.*, vol. 37, pp. 31–43 (1974).

Gottschalk, et al., "Chemically Crosslinked Lactate Dehydrogenase: Stability and Reconstitution after Glutaraldehyde Fixation," *Biotechnology and Applied Biochemistry*, vol. 9, No. 5, pp. 389–400 (Oct. 1987).

Hoshino, et al., "A study on the thermostability of microencapsulated glucose oxidase," *J. Microencapsulation*, vol. 6, No. 2, pp. 205–211 (1989).

Ichiba, et al., "Cation–induced thermostability of yeast and *Escherichia coli* pyrophosphatases," *Biochem. Cell Biol.*, vol. 66, pp. 25–31 (Jan. 1988).

Kokufuta, et al., "Useful of Polyelectrolyte Complex–Stabilized Calcium Alginate Gel for Entrapment of β–Amylase", *Biotechnology and Bioengineering*, vol. 32, pp. 756–759 (1988).

Laurence, "Fluorescence Techniques for the Enzymologist", *Methods in Enzymology*, vol. 4, S. P. Colowick and N.O. Kaplan, Eds., *Academic Press*, New York, 1957.

Lenders, et al. "Chemical Stabilization of Glucoamylase from *Aspergillus niger* against Thermal Inactivation," *Biotechnology and Bioengineering*, vol. 31, pp. 267–277 (1988).

Leonowicz, et al., "Improvement in stability of an immobilized fungal laccase," *Applied Microbiology and Biotechnology*, vol. 29, No. 2–3, pp. 129–135 (1988).

Mecke, "Hydrogen Peroxide Plasma—an Interesting Microbiocidal Concept", Hygiene + Medizin, 1992:17:pp. 537–543.

Olsen, et al. "Improvement of bacterial β–glucanase thermostability by glycosylation," *Journal of General Microbiology*, vol. 137, pp. 579–585 (1991).

Redway, et al., "Effect of Carbohydrates and Related Compounds on the Long–Term Preservation of Freeze–Dried Bacteria," *Cryobiology*, vol. 11, pp. 73–79 (1974).

Roth, "Fluorimetric Assay of Enzymes", *Methods of Biochemical Analysis*, vol. 17, D. Block, Ed., *Interscience Publishers*, New York, 1969.

Rutala et al., "Comparative evaluation of the sporicidal activity of new low–temperature sterilization technologies: Ethylene oxide, 2 plasma sterilization systems, and liquid peracetic acid", *AJIC*, vol. 26, No. 4, Aug. 1998, pp. 393–398.

Smith, et al., "Effect of Environmental Conditions during Heating on Commercial Spore Strip performance," *Applied and Environmental Microbiology*, vol. 44, No. 1, pp. 12–18 (Jul. 1982).

Srivastava, R., "Studies on stabilization of amylase by covalent coupling to soluble polysaccharides," *Enzyme Microb. Technol.*, vol. 13, No. 2, pp. 164–170 (Feb. 1991).

Srivastava, R., "Effect of glycosylation of bacterial amylase in stability and active site conformation," *Indian Journal of Biochemistry & Biophysics*, vol. 28, No. 2, pp. 109–113 (Apr. 1991).

Sugiyama, H., "Studies on Factors Affecting the Heat Resistance of Spores of *Clostridium botulinum*," *Journal of Bacteriology*, vol. 62, pp. 81–96 (1951).

Suwa, et al., "Effects of food emulsifiers on spoilage of canned coffee caused by thermpohilic spore–forming bacteria", (1988), pp. 706–708.

Toda, "Antimicrobial activity of polyglycerol fatty acid esters and their use in foods" (1988), pp. 69–74.

Torchilin, et al., "Stabilization of Subunit Enzymes by Intramolecular Crosslinking with Bifunctional Reagents," *Annals of New York Academy of Sciences*, vol. 434, pp. 27–30 (1984).

Udenfriend, "Fluorecence in Enzymology", *Fluorescence Assay in Biology and Medicine, Academic Press*, New York, pp. 312–348 (1962).

Vesley, et al., "Fluorimetric Detection of a *Bacillus stearothermophilus* Spore–Bound Enzyme, α–D–Glucosidase, for Rapid Indication of Flash Sterilization Failure," *Applied and Environmental Microbiology*, vol. 58, pp. 717–719 (Feb. 1992).

* cited by examiner

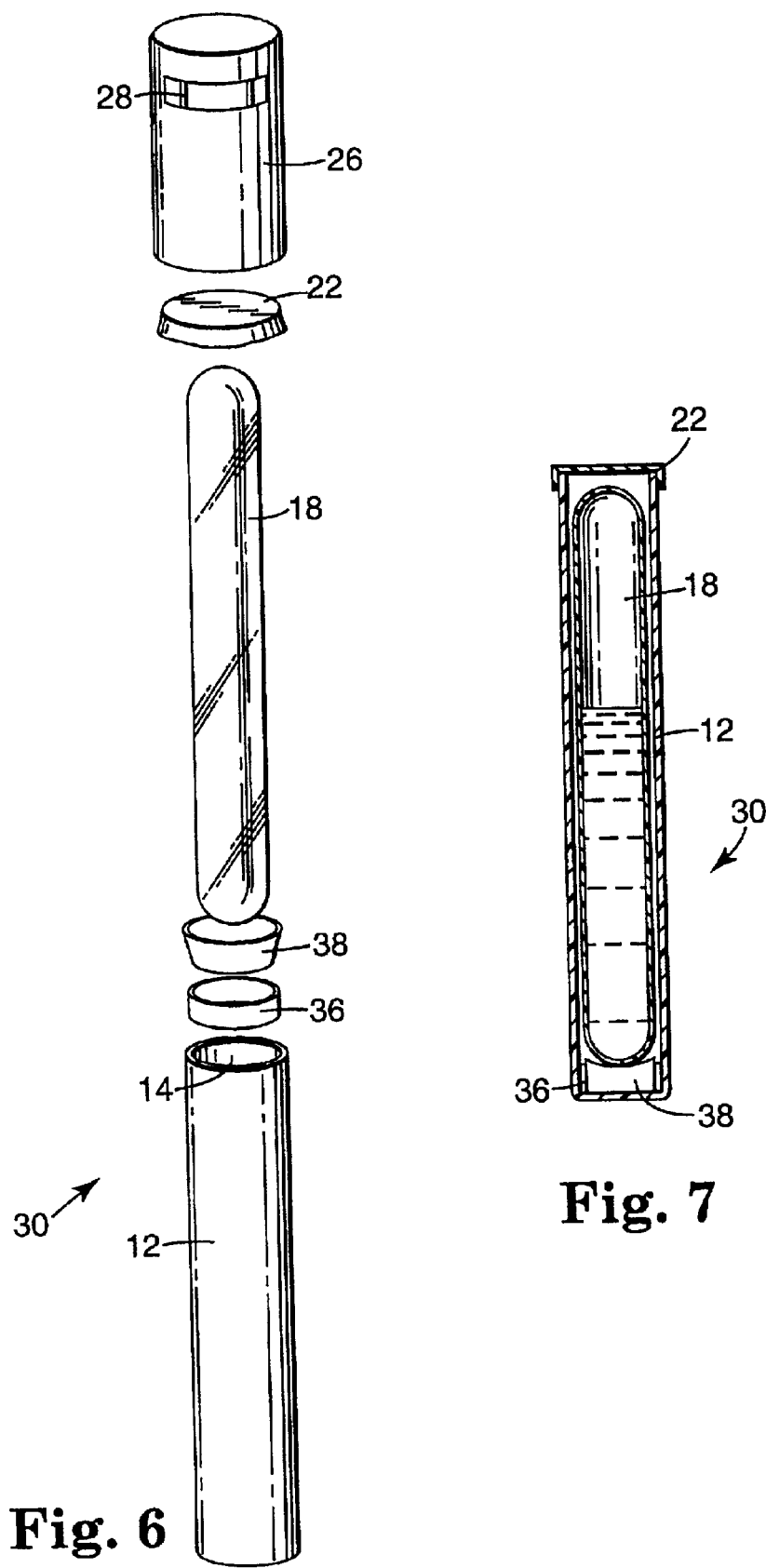

STERILIZATION INDICATOR WITH CHEMICALLY STABILIZED ENZYME

CROSS-REFERENCE TO OTHER APPLICATIONS

This application is a divisional of U.S. application Ser. No. 09/228,712, filed Jan. 12, 1999, now U.S. Pat. No. 6,355,448 which is a continuation-in-part of U.S. patent application Ser. No. 09/088,859, filed Jun. 2, 1998, abandoned.

FIELD OF THE INVENTION

The present invention relates to sterilization indicators for testing the effectiveness of a sterilization procedure, and in particular to sterilization indicators that measure the activity of an enzyme whose activity is correlated with the survival of microorganisms.

BACKGROUND

Sterilization indicators provide a means for determining whether a sterilizing machine, such as those used to sterilize surgical instruments in hospitals, is functioning properly and killing microorganisms that are present in the sterilization chamber during a sterilization procedure.

Biological indicators are recognized in the art as providing an accurate and precise means for testing the effectiveness of a sterilization procedure. Conventional biological indicators gauge the effectiveness of a sterilization procedure by monitoring the survival of a test microorganism contained within the biological indicator that is many times more resistant to the sterilization process than most organisms that would ordinarily be present by natural contamination. The biological indicator is exposed to a sterilization cycle and then incubated under conditions that will promote the growth of any surviving test microorganisms. If the sterilization cycle fails, the biological indicator generates a detectable signal indicating that the biological specimen survived. The detectable signal is commonly an indication such as a color change or the emission of a luminescent or fluorescent signal.

One well-known type of biological indicator employs spores from bacteria or fungi, which are very resistant to sterilization, to test the effectiveness of a sterilization procedure. U.S. Pat. No. 3,661,717 (Nelson) discloses a self-contained biological indicator for monitoring the effectiveness of a sterilization procedure by measuring the survival of a test population of spores. The biological indicator has an outer tube made of a compressible, plastic material and a sealed inner tube made of a breakable material such as glass. A bacteria impermeable, gas transmissive covering on the outer tube allows sterilant to enter the outer tube during a sterilization procedure. Live spores on a piece of carrier material are located between the walls of the outer tube and the inner tube. The inner tube contains a growth medium that stimulates the growth of live spores. During the sterilization procedure sterilant enters the outer tube through the cap and contacts the spores on the carrier strip. After the sterilization procedure, the inner tube is crushed by compressing the outer tube, releasing the growth media and bringing it into contact with the spores on the carrier strip. The indicator is then incubated under conditions that stimulate spore growth. If the sterilization procedure is ineffective, surviving spores will grow out and cause a pH indicator in the growth medium to change color, indicating that the sterilization cycle failed to kill the test population of microorganisms and may have failed to kill contaminating microorganisms present in the sterilizer load. Although biological indicators that rely on the growth of spores are accurate, they are slow, commonly requiring between 1 and 7 days to provide final results. During this incubation period the goods exposed to the sterilization procedure should preferably be quarantined until final indicator results are obtained. However, holding goods in quarantine for such a lengthy period of time requires a substantial commitment of space that could otherwise be used for other purposes, and complicates the efficient regulation of inventory.

Recently sterilization indicators have been developed that measure the effectiveness of a sterilization procedure by measuring the activity of an enzyme whose activity is correlated with the destruction of contaminating microorganisms during a sterilization procedure. Enzyme sterilization indicators are disclosed in U.S. Pat. Nos. 5,252,484 and 5,073,488. In contrast to biological indicators that measure spore growth alone, enzyme indicators provide a rapid answer, often in a matter of a few hours. The indicators have a compressible outer tube, a breakable inner tube, and a cap that is bacteria impermeable but gas trasmissive. Active enzyme is impregnated on a carrier strip located between the walls of the outer and inner containers, and a substrate that reacts with the active enzyme is contained within the sealed inner tube. During the sterilization procedure the sterilant enters the outer tube and contacts the active enzyme on the carrier strip. After the sterilization procedure, the inner vial is crushed and the enzyme strip is exposed to the substrate and incubated. If the sterilization procedure works properly, the enzyme is inactivated during the procedure and there is no detectable change following incubation. However, if the sterilization procedure is ineffective, the enzyme is not inactivated and will react with the substrate to form a detectable product. The enzyme-substrate product may be detectable as a color change or as a fluorescent or luminescent signal.

Dual rapid readout indicators are sterilization indicators that test the effectiveness of a sterilization procedure by measuring both enzyme activity and spore growth following exposure to a sterilization procedure. The enzyme system gives a rapid indication of the effectiveness of a sterilization cycle, which is then confirmed by measurement of spore outgrowth over a longer period of time. In a dual rapid readout indicator, the live spores utilized in the spore outgrowth portion of the indicator may also serve as the source of active enzyme for the enzyme activity portion of the assay. The rapid enzyme test measures the activity of an enzyme that is associated with the spores, and the spores themselves are then incubated to encourage the outgrowth of any spores that survived the sterilization procedure. 3M™ Attest™ 1291 and 1292 Rapid Readout Biological Indicators, available from 3M Company, St. Paul, Minn., are dual rapid readout indicators that test the effectiveness of a sterilization cycle by measuring both the activity of an enzyme associated with *Bacillus stearothermophilus* spores in the indicator and the survival of the spores themselves.

Although enzyme sterilization indicators are both rapid and accurate for testing the effectiveness of most steam sterilization procedures, the enzyme in an indicator may be prematurely inactivated before all of the contaminating microorganisms have been killed when certain prevacuum, or vacuum assisted, steam sterilization procedures are used. As a result, the sterilization indicator may provide an incorrect indication that the sterilization procedure was effective, or a "false negative" result. The existence of the premature inactivation problem has been detected with dual rapid readout indicators, which after exposure to a suspect sterilization procedure provide a negative result by the enzyme test and a contradictory positive result by the spore growth test. Premature inactivation of enzyme in sterilization indicators has been observed, and is known to be a problem, with 121° C. prevacuum sterilization cycles in which a vacuum is drawn in the sterilization chamber before stream is introduced. Although the precise mechanism underlying this problem is not known with certainty, it is believed that it may be caused by condensed sterilant contacting the enzyme and inactivating it.

Premature inactivation of enzyme has also been observed in dual rapid readout indicators that have been exposed to hydrogen peroxide plasma sterilization procedures. Sterilization processes using hydrogen peroxide plasma are known in the art and are described, for example, in U.S. Pat. No. 4,643,876, issued to Jacobs et al. Plasma refers to the portion of the gas or vapors of a sterilant that includes electrons, ions, free radicals, dissociated atoms and molecules that are produced when an electrical field is applied to the sterilant, and includes any radiation produced by the sterilant after application of the electrical field. In hydrogen peroxide plasma sterilization procedures, a vacuum is typically drawn in a sterilization chamber and hydrogen peroxide vapor is injected and allowed to diffuse throughout the chamber and contact the surfaces of all items that are intended to be sterilized. A vacuum is then drawn to remove the hydrogen peroxide vapor, and a plasma is generated within the chamber by an electrical power source, such as a radio frequency (RF) power source. The power is continued for a period of time sufficient to create a plasma that kills any microorganisms within the chamber. The precise mechanism responsible for premature inactivation in hydrogen peroxide plasma sterilization procedures is not known.

Efforts have been made in the art to prevent premature inactivation of enzyme in sterilization indicators. Commonly assigned U.S. patent application Ser. No. 08/954,218 (Albert) discloses a protective housing that impairs the premature inactivation of enzyme in an enzyme indicator or a dual rapid readout indicator by preventing condensed sterilant from contacting the indicator. The protective housing includes a tube to contain a biological indicator and a cap assembly designed to prevent condensed sterilant from contacting the biological indicator within the tube. The cap assembly includes an aperture through which non-condensed sterilant may enter the housing to contact the biological indicator. An absorbent material within the cap assembly retains condensed sterilant and inhibits fluid from entering the tube and contacting the biological indicator, yet allows noncondensed sterilant to enter the housing. Thus, the Albert application prevents premature inactivation indirectly, by providing a physical barrier that prevents condensed sterilant from contacting the enzyme.

There is a need in the art for an enzyme-based sterilization indicator in which the enzyme is made resistant to premature inactivation by a chemical treatment.

SUMMARY OF THE INVENTION

The present invention addresses the problem of premature inactivation of enzymes in enzyme-based sterilization indicators by providing a sterilization indicator in which the source of active enzyme has been treated with a sterilant-resistant chemical. The sterilization indicator of the invention comprises a source of active enzyme, a sterilant-resistant chemical associated with the source of active enzyme, and a substrate that is capable of reacting with the active enzyme to form an enzyme-modified product that provides a detectable indication of the failure of a sterilization procedure.

In one embodiment of the invention, the sterilant-resistant chemical may be a polyglycerol alkyl ester or a polyglycerol alkyl ether. In another embodiment the sterilant-resistant chemical may be an ethoxylated polyhydric alcohol ester or an ethoxylated polyhydric alcohol ether.

In a preferred embodiment of the invention, the sterilization indicator is a self-contained biological indicator in which the enzyme has been chemically treated to enhance its resistance to premature inactivation. The biological indicator comprises a compressible outer container, a breakable inner container, a source of active enzyme associated with a sterilant-resistant chemical, and a substrate that is capable of reacting with the enzyme to form an enzyme-modified product that provides a detectable indication of the failure of a sterilization procedure. The outer container has at least one opening to allow sterilant to enter the outer container during a sterilization procedure. The inner container is sealed at both ends and contains the reactive substrate. The source of active enzyme is located between the walls of the outer container and the inner container.

The invention also provides a method for testing the effectiveness of a sterilization procedure using a sterilization indicator made with spores that have been treated with a sterilant-resistant chemical. The method comprises the steps of providing a sterilization indicator, subjecting the sterilization indicator to a sterilization procedure, combining the enzyme and substrate within the sterilization indicator, and examining the sterilization indicator for a detectable signal indicating the failure of the sterilization cycle.

In addition, the invention provides a sterilization indicator for specific use in a hydrogen peroxide plasma sterilization procedure in which the enzyme has been chemically treated to enhance its resistance to premature inactivation. The sterilization indicator includes a source of active enzyme, a sterilant-resistant chemical associated with the source of active enzyme, and a substrate that is capable of reacting with the active enzyme to form an enzyme-modified product that provides a detectable indication of the failure of a sterilization procedure. In this embodiment, the sterilant-resistant chemical is preferably selected from the group consisting of decaglyceryl decaoleate, decaglycerol pentaoleate, tetraglycerol monooleate, decaglyceryl trioleate, decaglycerol hexaoleate, hexaglycerol dioleate, polyoxyethylene (60) glycerol monostearate, polyoxyethylene (20) sorbitan monostearate, and hexaglyn di-stearate.

In a preferred embodiment, the sterilization indicator for use in hydrogen peroxide plasma procedures is a self-contained biological indicator. The indicator employs a source of active enzyme that has been chemically treated to enhance its resistance to premature inactivation. The self-contained biological indicator comprises a compressible outer container, a breakable inner container, a source of active enzyme associated with a sterilant-resistant chemical, and a substrate that is capable of reacting with the enzyme to form an enzyme-modified product that provides a detectable indication of the failure of a sterilization procedure. The outer container has at least one opening to allow sterilant to enter the outer container during a sterilization procedure. The inner container is sealed at both ends and contains the reactive substrate. The source of active enzyme is located between the walls of the outer container and the inner container.

The hydrogen peroxide plasma indicators of the invention may be used either alone or as part of a test pack. The invention provides two embodiments of a test pack for use with the sterilization indicators: a non-challenge test pack and a lumen-challenge test pack.

The non-challenge test pack holds the sterilization indicator in place but provides no increased resistance, or "challenge," to a sterilization procedure. The non-challenge test pack includes a thermally-resistant plastic tray, a sterilization indicator, and a thermally-resistant plastic lid. The tray includes an elevated rim defining the perimeter of the tray and a recessed trough for holding a sterilization indicator. The rim includes a plurality of grooves that extend through the rim to the recessed trough. When the lid is placed on the tray, it forms a substantially sterilant-impermeable seal with the rim surface and forms a plurality of channels with the grooves in the rim. When the non-challenge test pack is subjected to a sterilization procedure, sterilant travels through the channels and contacts the sterilization indicator within the tray.

The lumen-challenge test pack increases the resistance of the sterilization indicator to a level that is equivalent to the resistance that would be experienced if the sterilization indicator were placed within a lumen having a defined length and cross-sectional area. The lumen-challenge test pack comprises a plastic tray for holding the sterilization indicator, a sterilization indicator and a plastic lid. The tray includes a substantially planar surface with an edge that defines the outer perimeter of the tray, a recessed trough for holding the sterilization indicator, and a recessed groove of a defined length and cross-sectional area extending through the trough and penetrating the edge of the tray at two points. When the lid is placed on the tray, a substantially impermeable seal is formed between the lid and the substantially planar surface of the tray, and a lumen path is formed between the lid and the recessed groove of the tray. During a sterilization procedure, sterilant may enter the test pack through the lumen path and contact the sterilization indicator.

BRIEF DESCRIPTION OF THE FIGURES

FIG. 6 is an exploded view of an alternative preferred embodiment of the sterilization indicator of the invention.

FIG. 7 is cross-sectional view of the device shown in FIG. 6.

DETAILED DESCRIPTION OF THE INVENTION

The sterilization indicators of this invention address a problem experienced with biological indicators that use enzymes to test the effectiveness of sterilization procedures, such as the enzyme sterilization indicators and dual rapid readout indicators described in U.S. Pat. No. 5,252,484 and U.S. Pat. No. 5,073,488, which are incorporated in their entirety herein by reference. In particular, the sterilization indicators of the present invention are designed to alleviate the problem of premature inactivation of enzyme in a sterilization indicator. This objective is accomplished by treating the spores used as a source of active enzyme with a sterilant-resistant chemical before assembling the indicators.

Although enzyme sterilization indicators are used in several different types of sterilization cycles, premature inactivation of enzyme is not a problem with all of them. It is primarily a problem with regard to a particular class of pre-vacuum sterilization procedure in which a vacuum is drawn in the sterilization chamber before steam is introduced. A pre-vacuum sterilization cycle is one in which a vacuum-driven conditioning phase is used before the chamber reaches sterilization temperature.

Figure 3:
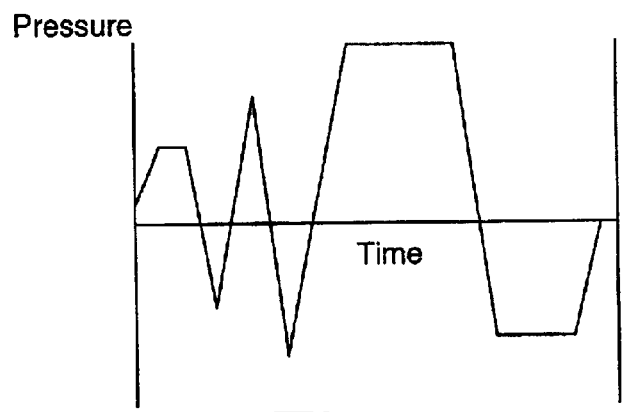
FIG. 3 is a graph depicting the change in pressure over time in a pre-vacuum steam sterilization cycle in which steam is introduced into the sterilization chamber before a vacuum is drawn.
Figure 4:
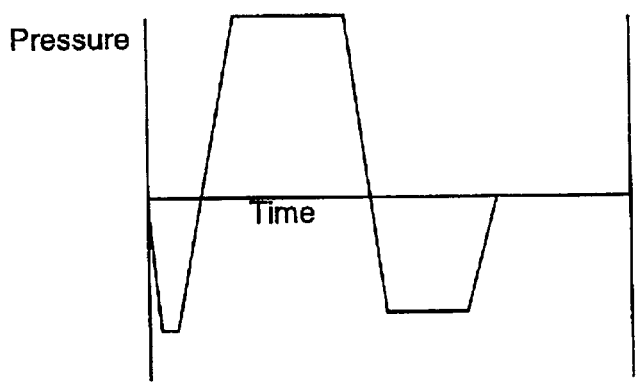
FIG. 4 is a graph depicting the change in pressure over time in a pre-vacuum steam sterilization cycle in which a vacuum is drawn in a sterilization chamber before steam is injected.
Figure 5:
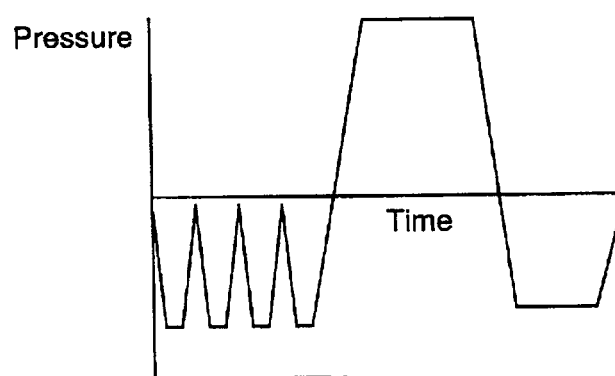
FIG. 5 is a graph depicting the change in pressure over time in a pre-vacuum steam sterilization cycle in which a series of vacuum pulses are drawn in the chamber before steam is injected.

FIGS. 3–5 are graphs that depict the change in pressure over time in three different pre-vacuum sterilization procedures that are commonly used. The procedure represented in FIG. 3 is one that is not prone to cause premature inactivation of enzymes and false negatives in enzyme sterilization indicators. In this procedure, steam is injected into the sterilization chamber before a vacuum is exerted. The initial pressure during the sterilization cycle is positive relative to atmospheric pressure as steam is injected into the sterilization chamber but then becomes negative relative to atmospheric pressure as a vacuum is exerted in the chamber. When an enzyme sterilization indicator is exposed to a sterilization cycle such as the one shown in FIG. 3, the enzyme should be inactivated shortly after the spores have been killed. In the pre-vacuum steam procedures that are most commonly used in the United States, steam is injected into the sterilization chamber before a vacuum is exerted.

In contrast, FIGS. 4–5 depict two pre-vacuum steam sterilization procedures in which a vacuum is drawn in the sterilization chamber before steam is introduced. These procedures, which are commonly used in Europe, are prone to cause the premature inactivation of enzyme and false negatives in enzyme sterilization indicators. In the sterilization procedure represented in FIG. 4, the pressure in the sterilization chamber becomes negative relative to atmospheric pressure as a vacuum is drawn prior to the introduction of steam. In the sterilization cycle represented in FIG. 5, four pulses of vacuum are drawn in the chamber followed by steam injection before the chamber reaches sterilization temperature. Although the precise mechanism of the inactivation of enzyme in these cycles is not known with certainty, and the applicant does not wish to be bound by any particular theory of operation, it is believed that the enzyme may be inactivated when it is contacted with condensed sterilant.

Figures 1, 2:
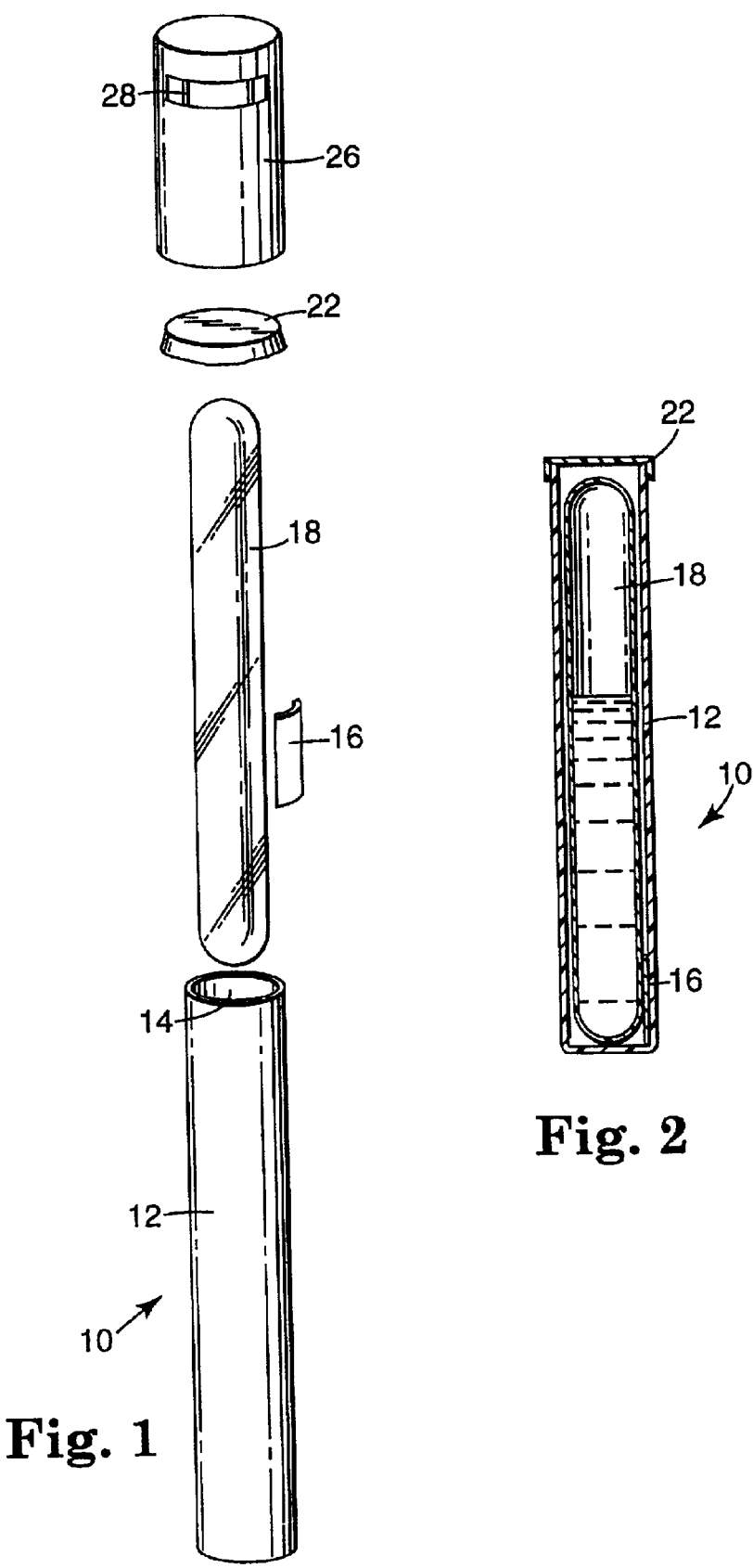
FIG. 1 is an exploded view of a preferred embodiment of a sterilization indicator of the invention.
FIG. 2 is a cross-sectional view of the device shown in FIG. 1.

The sterilization indicator of the invention is shown in FIGS. 1 and 2. The sterilization indicator 10 includes nesting containers that separate the various components of the system from each other until after the sterilization cycle is complete. The sterilization indicator 10 includes an outer tube 12, a sealed inner tube 18 and a vented cap 26. Outer tube 12 is preferably made of a compressible plastic. Inner tube 18 is made of glass or some other frangible material.

Closure member 22 is preferably a bacteria impermeable, gas transmissive barrier that fits over the open end 14 of outer tube 12. Carrier strip 16 includes on its surface a source of active enzyme, either microorganism spores or a purified enzyme, and is disposed between the walls of the inner tube 18 and the outer tube 12. The source of active enzyme has been treated with a sterilant-resistant chemical to prevent premature inactivation of the enzyme during a sterilization cycle. Inner tube 18 contains a substrate that reacts with the enzyme on carrier strip 16 and creates a detectable signal if the sterilization procedure is ineffective.

During a sterilization procedure sterilant enters the outer tube 12 through the vents 28 on cap 26 and contacts the source of active enzyme on carrier strip 16 but does not contact the substrate solution in the sealed inner tube 18. After the sterilization cycle the sides of the outer tube 12 are compressed, breaking the inner tube 18 and bringing the enzyme and substrate into contact with each other. The sterilization indicator is then incubated for a period of time sufficient for any remaining active enzyme to react with the substrate to form an enzyme-modified product that produces a detectable signal, such as luminescence, fluorescence or a color change, indicating that the sterilization procedure may have been ineffective.

In a preferred embodiment of the sterilization indicator 10 of the invention, the source of active enzyme on carrier strip 16 is a live microorganism, such as a bacterial or fungal spore. In the most preferred embodiment, spores are the source of active enzyme, and the sterilization indicator 10 is a dual rapid readout indicator that monitors the effectiveness of a sterilization procedure by measuring both enzyme activity and spore outgrowth. In this embodiment, the inner tube 18 contains spore growth medium and enzyme substrate. After the sterilization cycle is complete, the inner tube 18 is broken, and the carrier strip 16 is exposed to its contents and incubated. The enzyme test produces visible results within a few hours, and the live microorganism growth test confirms these results within 7 days.

The theory underlying the operation of enzyme indicators is that the inactivation of the enzyme will be correlated with the death of test microorganisms in the indicator. The enzyme selected for use in a biological indicator must be at least as resistant to a sterilization procedure as microorganisms that are likely to be present as contaminants, and preferably more resistant than such microorganisms. The enzyme should remain sufficiently active to form a detectable enzyme-substrate product after a sterilization cycle that fails to kill contaminating microorganisms, yet be inactivated by a sterilization cycle that kills contaminating microorganisms.

Enzymes and substrates that are suitable for use in the sterilization indicators of the invention are described in U.S. Pat. No. 5,252,484 and U.S. Pat. No. 5,073,488. Suitable enzymes include enzymes derived from spore-forming microorganisms, such as *Bacillus stearothermophilus* and *Bacillus subtilis*. Enzymes from spore-forming microorganisms that are useful in the biological indicators of the invention include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-B-glucosaminodase, beta-D-cellobiosidase, alanine aminopeptidase, proline aminopeptidase and a fatty acid esterase, derived from spore forming microorganisms.

Chromogenic and fluorogenic substrates that react with enzymes to form detectable products, and that are suitable for use in the sterilization indicator of the invention, are well known in the art. (M. Roth, *Methods of Biochemical Analysis*, Vol. 17, D. Block, Ed., Interscience Publishers, New York, 1969, p. 89; S Udenfriend, *Fluorescence Assay in Biology and Medicine*, Academic Press, New York, 1962, p. 312; D. J. R. Lawrence, *Fluorescence Techniques for the Enzymologist*, Methods in Enzymology, Vol. 4, S. P. Colowick and N. O. Kaplan, Eds., Academic Press, New York, 1957, p. 174, incorporated herein by reference). These substrates may be classified in two groups based on the manner in which they create a visually detectable signal. The substrates in the first group react with enzymes to form enzyme-modified products that are themselves chromogenic or fluorescent. The substrates in the second group form enzyme-modified products that must react further with an additional compound to generate a color or fluorescent signal.

Microorganisms that are particularly preferred to serve as the sources of active enzyme in the indicators of the invention include *Bacillus stearothermophilus* and *Bacillus subtilis*, which are microorganisms that are commonly used as test microorganisms in spore outgrowth indicators utilized to monitor sterilization procedures. Where dual rapid readout indicators are used, these microorganisms may serve as both the source of active enzyme in the rapid enzyme test and the test microorganism for the spore outgrowth test. *Bacillus stearothermophilus* is particularly preferred for monitoring both steam and hydrogen peroxide plasma sterilization procedures. *Bacillus subtilis* is particularly preferred for monitoring ethylene oxide sterilization procedures and may be used to monitor hydrogen peroxide plasma sterilization procedures. 3M™ ATTEST™ 1291 and 1292 Rapid Readout Indicators, commercially available from 3M Company, St. Paul, Minn., are dual rapid readout indicators that measure the activity of the enzyme alpha-D-glucosidase, from *Bacillus stearothermophilus*, and the growth of *B. stearothermophilus* live spores.

The sterilant-resistant chemical used in the sterilization indicator of the invention may be any chemical that, when associated with a source of active enzyme, increases the resistance of the enzyme to sterilant so that premature inactivation is avoided. When the source of active enzyme used in the sterilization indicator 10 is the spore of a microorganism, such as *Bacillus stearothermophilus* or *Bacillus subtilis*, the spores are preferably treated with the sterilant-resistant chemical before they are placed on the carrier strip 16.

The sterilant-resistant chemical is preferably one that, when associated with the source of active enzyme in the indicator, will prevent the enzyme from being inactivated by a sterilization procedure that is ineffective in that it fails to kill contaminating microorganisms present in the sterilization chamber. Where the sterilization indicator is a dual rapid readout indicator that measures both enzyme activity and spore outgrowth, the sterilant-resistant chemical is preferably one that, when associated with the source of active enzyme, will prevent the enzyme from being inactivated by a sterilization procedure that is not sufficient to kill the test microorganisms used in the indicator for the outgrowth portion of the sterility test.

When a source of active enzyme is treated with the sterilant-resistant chemicals of the invention, the enzyme will preferably have sufficient activity following a sterilization cycle which is sublethal to at least one test microorganism commonly used to monitor sterilization, to react with an effective amount of substrate for the enzyme to produce a detectable enzyme-modified product within less than twenty-four hours; yet the enzyme will have activity which is reduced to background following a sterilization cycle which is lethal to the test microorganism. Most preferably, a source of active enzyme treated with the sterilant-resistant chemicals of the invention, when subjected to a sterilization cycle which would be just sufficient to decrease the population of $1 \times 10^6$ test microorganisms to zero, as measured by lack of outgrowth of the microorganism, has activity equal to background, as measured by reaction with an effective amount of a substrate capable of reacting with the active enzyme to produce a detectable enzyme-modified product; yet when subjected to a sterilization cycle sufficient to decrease the population of $1 \times 10^6$ of the test microorganisms by at least about 1 log but less than about 6 logs, has activity greater than background, as measured by reaction with an effective amount of the substrate.

In a preferred embodiment of the invention the sterilant-resistant chemical is a surfactant having hydrophobic regions and hydrophilic regions on the same molecule and having the general structure $R_aL_b$, where R represents a hydrophobic group, L represents a hydrophilic group, and a and b are each numbers from 1 to 4. R is preferably an alkyl group of at least 6 carbon atoms, more preferably at least 8 carbon atoms and most preferably at least 12 carbon atoms. L may suitably be selected from the group including carboxyl groups and their salts; hydroxyl groups; sulfonate groups and their salts; sulfate groups and their salts; phosphates; phosphonates; zwitterionic groups; ethylene oxide/propylene oxide copolymer groups; esters or ethers of sorbitan or a polyalkoxylated sorbitan group; polyalkoxylated fatty acid esters or ethers; betaines; amide groups having the structure —NHC(O)R''' or —C(O)NHR''', where R''' is hydrogen or an alkyl group of 1–10 carbon atoms optionally substituted in available positions by N, O, and S atoms; ester groups of short chain alcohols or acids; ether groups; polyglycerol esters or ether groups having 1–20 glycerol units, preferably 2–12 glycerol units and more preferably 3–10 glycerol units; secondary amine groups; and tertiary amine groups.

In a preferred embodiment of the invention the sterilant-resistant chemical may include a surfactant and a hydrophobic additive. The hydrophobic additives are defined as being non-water soluble and non-self dispersible in water, and as such require emulsification by a surfactant. Suitable hydrophobic additives include compounds that are waxes and oils at room temperature. Hydrophobic additives that are appropriate for use as part of the sterilant-resistant chemical include short chain alkyl or aryl esters (C1–C6) of long chain (straight or branched) alkyl or alkenyl alcohols or acids (C8–C36) and their polyethoxylated derivatives; short chain alkyl or aryl esters (C1–C6) of C4–C12 diacids or diols, optionally substituted in available positions by —OH; alkyl or aryl C1–C9 esters of glycerol, pentaerythritol, ethylene glycol; C12–C22 alkyl esters or ethers of polypropylene glycol; C12–C22 alkyl esters or ethers of polypropylene glycol/polyethylene glycol copolymer; poly ether polysiloxane copolymers; cyclic dmethicones; polydialkylsiloxanes; polyaryl/alkylsiloxanes; long chain (C8–C36) alkyl and alkenyl esters of long straight or branched chain alkyl or alkenyl alcohols or acids; long chain (C8–C36) alkyl or alkenyl amides of long straight or branched chain (C8–C36) alkyl or alkenyl amines or acids; hydrocarbons including straight and branched chain alkanes and alkenes, such as squalene, squalane, polyethylene waxes, lanolin, petrolatum and mineral oil; polysiloxane polyalkylene copolymers; dialkoxy dimethyl polysiloxanes; short chain alkyl or aryl esters (C1–C6) of C12–C22 diacids or diols, optionally substituted in available positions by OH; and C12–C22 alkyl and alkenyl alcohols. Suitable hydrophobic additives include isostearyl alcohol, cetyl alcohol, diisopropyl adipate, squalane, mineral oil, isopropyl myristate, dimethicone, lanolin and petrolatum.

In another preferred embodiment the sterilant-resistant chemical is a polyglycerol alkyl ester or ether, or a mixture of chemicals including a polyglycerol alkyl ester or ether. In another preferred embodiment, the sterilant-resistant chemical is an ethoxylated glycerol ester or ether, or a mixture of chemicals including an ethoxylated glycerol ester or ether. The sterilant-resistant chemical may also include, in a preferred embodiment, decaglycerol, sorbitol or mixtures of chemicals including one of them. In another preferred embodiment, the sterilant-resistant chemical is a mixture of decaglycerol monostearate and sorbitol.

Polyglycerol alkyl esters or ethers that may be used as sterilant-resistant chemicals may be selected from chemicals having the formula:

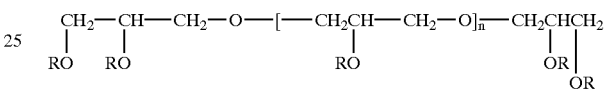

Polyglyerol Alkyl Esters or Ethers

In this formula, n is 0 to 50; R is either H or an ether or ester group of the formula R' or

where R' can be H or a C1 to C50 straight chain or branched alkyl, alkylene, aralkyl or alkenyl group, which can be substituted in available positions by N, O and S. The polyglycerol portion may contain linear, branched or cyclic isomers, and is generally available in a broad range of molecular weights.

Polyglycerol alkyl esters or ethers that are preferred for use as sterilant-resistant chemicals in the invention include decaglyceryl monostearate, hexaglyceryl monostearate, tetraglyceryl monostearate, hexaglyceryl polyricinolate, decaglyceryl monolaurate, tetraglyceryl monooleate, decaglyceryl trioleate, decaglyceryl monooleate, decaglyceryl dipalmitate, hexaglyceryl distearate, decaglyceryl monooleate, decaglyceryl monomyristate, decaglyceryl monoisostearate, decaglyceryl diisostearate, hexaglycerol monolaurate, tetraglyceryl monooleate, and decaglyceryl trioleate.

Ethoxylated glycerol esters or ethers that may be used as sterilant-resistant chemicals may be selected from chemicals having the formula:

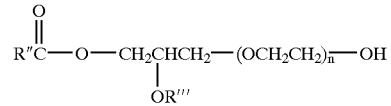

Ethoxylated Glycerol Esters or Ether

In this formula, n is 0 to 50; R'' can be a C5 to C50 straight chain or branched alkyl, alkylene, aralkyl or aralkenyl group, which can be substituted in available positions by N, O and S; and R''' can be H or a C1 to C50 straight chain or branched alkyl, alkylene, aralkyl or alkenyl group, which can be substituted in available positions by N, O and S. Preferably R'' is a linear alkyl group of 6–20 carbons, n is 2 to 10, and R''' is a linear alkyl group of 6 to 20 carbons.

Ethoxylated glycerol esters or ethers that are particularly preferred for use as sterilant-resistant chemicals include glycereth-7-diisononanoate, and polyoxythethylene (5) glyceryl monostearate.

The sterilization indicators 10 of the invention are prepared according to the methods described in U.S. Pat. No. 5,252,484 and U.S. Pat. No. 5,073,488. When spores are used as the source of active enzyme in the sterilization indicator 10, the spores are grown on culture plates and then removed and washed by sequential suspension in water and centrifugation. The spores are then suspended in a solution containing the sterilant-resistant chemical and transferred to the carrier strip 16 by pipetting. Although any number of spores may be applied to a carrier strip 16 used in the sterilization indicator 10, in the preferred embodiment of the invention $1 \times 10^6$ spores are transferred to each strip.

A person of ordinary skill in the art will be able to ascertain without undue experimentation the optimal concentrations of the various sterilant-resistant chemicals used in practicing the invention. The invention is therefore not limited to the use of the identified chemicals at any specific concentration or range of concentrations. However, the preferred concentrations of the sterilant-resistant chemicals are as follows:

| Sterilant-Resistant Chemical | Preferred Range (mg/ml) |
|---|---|
| Decaglyceryl monostearate | 10–100 |
| Hexaglyceryl monostearate | 5–30 |
| Tetraglyceryl monostearate | 5–40 |
| Decaglyceryl monolaurate | 50–100 |
| Hexaglyceryl monolaurate | 50–100 |
| Tetraglyceryl monooleate | 50–100 |
| Decaglyceryl trioleate | 50–100 |
| Decaglyceryl monoleate | 100 |
| Decaglyceryl dipalmtate | 50–100 |
| Hexaglyceryl distearate | 25–100 |
| Decaglyceryl monooleate | 100 |
| Decaglyceryl monomyristate | 100 |
| Decaglyceryl monoisostearate | 50–100 |
| Decaglyceryl diisostearate | 50–100 |
| Glycereth-7-diisononanoate | 20–40 |
| Polyoxyethylene (5) glyceryl monostearate | 50–100 |
| Decaglycerol | 100 |
| Sorbitol | 100 |

The sterilization indicator of the invention may suitably be used to monitor the effectiveness of any type of sterilization procedure, including sterilization procedures that use steam, hydrogen peroxide vapor phase, hydrogen peroxide plasma, ethylene oxide gas, dry heat, propylene oxide gas, methyl bromide, chlorine dioxide, formaldehyde and peracetic acid (alone or with a vapor phase), and any other gaseous or liquid agents. More preferably, the biological indicator may be used to monitor the effectiveness of any sterilization procedures in which there is a risk that the enzyme will be prematurely inactivated during the sterilization cycle. Sterilization indicators of the invention are most preferably used to monitor the effectiveness of a steam sterilization process utilizing a conditioning phase in which a vacuum is drawn in the chamber before steam is introduced, such as those depicted by the graphs in FIGS. 4 and 5.

In another embodiment of the invention, the sterilization indicator 10 is made specifically for use in monitoring the effectiveness of hydrogen peroxide plasma sterilization procedures, by treating the source of active enzyme with one or more sterilant-resistant chemicals that are especially resistant to premature inactivation during the hydrogen peroxide plasma sterilization procedure. These indicators may be used either alone or as part of a test pack, which includes a tray and a lid in addition to the sterilization indicator. The design of the test pack may be adjusted, as discussed below, to provide the sterilization indicator with a variable amount of additional resistance to the hydrogen peroxide plasma procedure. In one embodiment, the test pack may provide no additional resistance relative to the resistance of the indicator when used alone; and in an alternative embodiment, the test pack may provide the indicator with additional resistance that is equivalent to the additional resistance the indicator would experience if placed within a lumen having a defined cross-sectional area and length.

The sterilization indicators of the invention may be used to monitor the effectiveness of any of the hydrogen peroxide plasma sterilization procedures known in the art, including, for example, the procedures described in U.S. Pat. No. 4,643,876.

In a preferred embodiment of the invention, the hydrogen peroxide plasma indicator of the invention is either an enzyme indicator or a dual rapid readout indicator, as described above, in which the source of active enzyme has been treated with one or more sterilant-resistant chemicals. Suitable sterilant-resistant chemicals include decaglyceryl decaoleate, decaglycerol pentaoleate, tetraglycerol monooleate, decaglyceryl trioleate, decaglycerol hexaoleate, hexaglycerol dioleate, polyoxyethylene (60) glycerol monostearate, polyoxyethylene (20) sorbitan monostearate and hexaglyn di-stearate.

Suitable sterilant-resistant chemicals may include sorbitan fatty acid esters and polyoxyethylene sorbitan fatty acid esters selected from compounds having the formula:

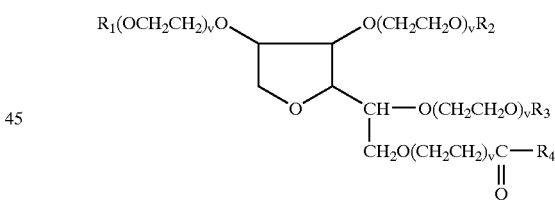

Sorbitan Fatty Acid Esters and Polyoxyethylene Sorbitan Fatty Acid Esters

In this formula, $R_1$, $R_2$ and $R_3$ can be H or

where $R_4$ and $R_5$ are straight or branched chain alkyl or alkenyl hydrocarbon chains of at least four carbon atoms, preferably at least 12 carbon atoms, and most preferably at least 16 carbon atoms; and v is 0–200 and preferably 2–30. A most preferred polyoxyethylene sorbitan fatty acid ester is polyoxyethylene (POE) (20) sorbitan monostearate.

In a preferred embodiment of the invention, the hydrogen peroxide plasma indicator is a dual rapid readout indicator in which the spores of a microorganism serve as both the source of active enzyme for the enzyme activity test, and the test microorganism for the spore outgrowth test. Suitable microorganisms include Bacillus stearothermophilus and Bacillus subtilis. In the most preferred embodiment, Bacillus stearothermophilus spores are used in the indicators.

The spores for use in hydrogen peroxide plasma indicators are treated with sterilant-resistant chemicals using the procedure detailed above. Cultured spores are removed from culture plates and washed by sequential suspension in water followed by centrifugation. A predetermined number of spores, preferably $1 \times 10^6$, are then suspended in a solution containing the sterilant-resistant chemical and transferred to the carrier strip 16. A person of ordinary skill in the art will be able to ascertain without undue experimentation the optimal concentrations of the various sterilant-resistant chemicals used in practicing the invention. Accordingly, the invention is not limited to the use of the identified chemicals at any specific concentration or range of concentrations. However, the preferred concentrations of the sterilant-resistant chemicals for use in hydrogen peroxide plasma sterilization procedures are as follows:

| Sterilant-Resistant Chemical | Preferred Range (mg/ml) |
| --- | --- |
| Decaglyceryl Decaoleate | 5–25 |
| Decaglycerol Pentaoleate | 10–50 |
| Tetraglycerol Monooleate | 10–50 |
| Decaglyceryl Trioleate | 10–50 |
| Decaglycerol Hexaoleate | 5–25 |
| Hexaglycerol Dioleate | 10–50 |
| Polyoxyethylene (60) Glycerol Monostearate | 10–50 |
| Polyoxyethylene (20) Sorbitan Monostearate | 10–50 |
| Hexaglyn Distearate | 10–50 |

Sterilization indicators for use with hydrogen peroxide plasma procedures are preferably prepared according to the methods discussed above and have the configuration of the indicator 10 shown in FIG. 1. However, when the indicator is to be used to monitor hydrogen peroxide plasma procedures, closure member 22 is preferably made of a high-density fiber material, such as TYVEK™ high-density polyethylene fiber material, commercially available from E. I. du Pont de NeMours and Co., Wilmington, Del.

In use, the sterilization indicator 10 is placed in the sterilization chamber and exposed to a hydrogen peroxide plasma sterilization procedure. Sterilant enters the indicator 10 through vent 28 and closure member 22, and contacts the source of active enzyme located on enzyme carrier 16. After the procedure is completed, the indicator 10 is removed from the sterilization chamber and the sides of the outer tube 12 are compressed, breaking the frangible inner tube 18 and releasing the enzyme substrate so that it may contact the source of enzyme on carrier strip 16. The sterilization indicator 10 is then incubated for a period of time sufficient for any active enzyme remaining in the indicator to react with the substrate and form an enzyme-modified product, which provides a detectable indication of the failure of the sterilization procedure. The enzyme-modified product may be detectable as fluorescence, luminescence or a color change. If the sterilization procedure is effective and all active enzyme has been inactivated, then no detectable signal is generated upon incubation.

In a more preferred embodiment of the sterilization indicator 30 for use in a hydrogen peroxide plasma sterilization procedure, shown in FIGS. 6–7, the enzyme carrier 36 is located within outer tube 12 near the closed end of the tube, and a barrier 38 is situated between the carrier strip 36 and the inner tube 18. The barrier is preferably a disc of polypropylene blown microfiber material having a weight of 200 g/sq. meter, commercially available as "THINSULATE™ 200-B brand Thermal Insulation" from 3M Company, St. Paul, Minn.

Figure 8:
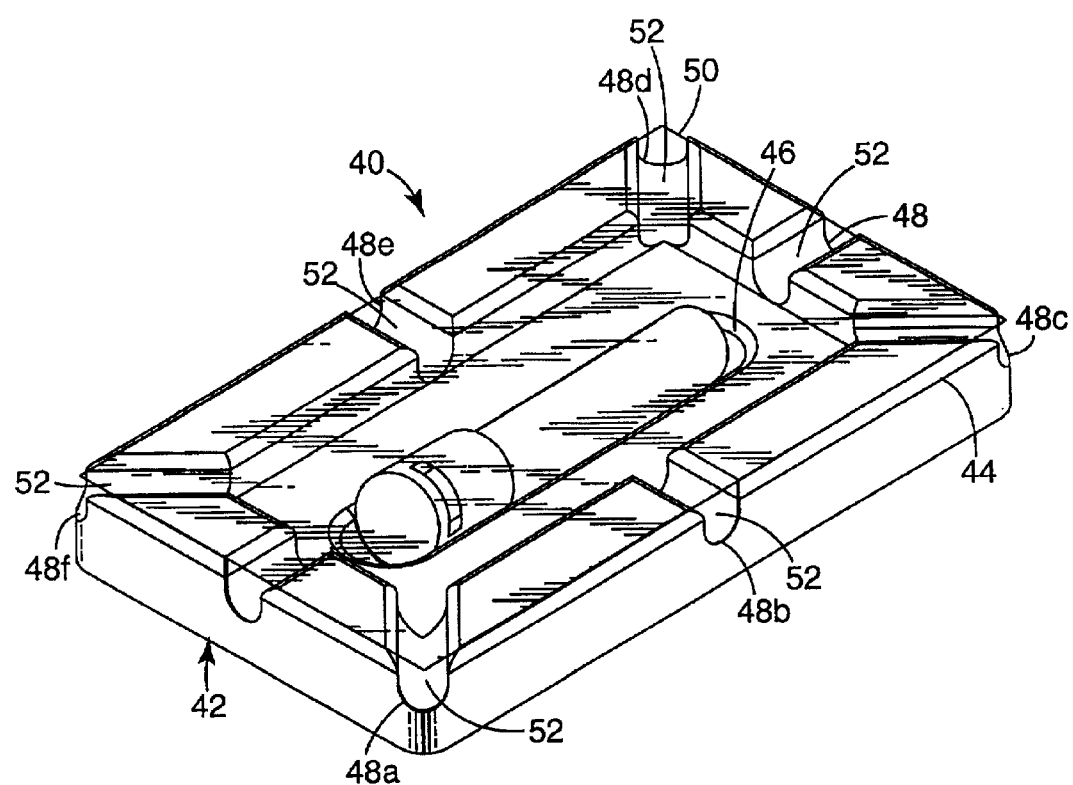
FIG. 8 is a perspective view of a preferred embodiment of the non-challenge test pack of the invention.

Any of the sterilization indicators of the invention 10, 30 may be used as part of a test pack. In one embodiment of the invention, shown in FIG. 8, non-challenge test pack 40 of the invention provides no additional resistance to the sterilization procedure above the resistance of the sterilization indicator 10 alone. The non-challenge test pack provides an advantage over the use of the indicator without a test pack in that it securely holds the sterilization indicator in a single position during the sterilization procedure. The non-challenge test pack thus alleviates a problem that occurs when sterilization indicators, which are typically small and prone to roll about, become displaced or misplaced in a load of materials during a sterilization procedure.

The non-challenge sterilization test pack 40 includes a plastic tray 42 for holding a sterilization indicator 10 and a plastic lid 50 that is associated with the tray 42 in such a manner that sterilant may freely enter the test pack and contact the sterilization indicator without any resistance other than the resistance provided by the sterilization indicator 10 itself. The plastic tray 42 may have any shape but is preferably rectangular or square. The plastic tray 42 has an elevated rim surface 44 that defines the perimeter of the tray and a recessed trough 46 for holding the sterilization indicator 10 in place during a sterilization procedure. A plurality of spaced-apart grooves 48a–48f are recessed into the rim surface 44 along the perimeter of the tray 42 and form a series of channels 52 with the surface of the lid 50. The channels should be large enough in cross-sectional area to conduct sterilant from the exterior of the test pack to the sterilization indicator 10 without creating any significant hindrance to the flow of the sterilant through the channel. In a preferred embodiment, the channels have a cross-sectional area equivalent to about the area of a circle with a diameter of 0.25 inches (0.635 cm), and there are six channels, one at each corner of the tray and one along each side. However, it will be readily apparent to one of skill in the art that both the number of channels and their dimensions may be altered without deviating from the scope of the invention.

Preferably, the lid 50 and the portions of the rim surface 44 that contact the lid 50 form a seal that is substantially impermeable to sterilant. Such a seal may preferably be formed by placing a layer of an adhesive between the surfaces of the lid 50 and the rim surface 44 that are in contact with each other. More preferably, the seal may be formed by heat-sealing the plastic lid 50 to the rim surface 44.

During a sterilization procedure the channels conduct sterilant from the sterilization chamber to the sterilization indicator 10 in the recessed trough 46. The sterilant then enters the indicator 10 and contacts the source of active enzyme, as previously described. The indicator 10 is then removed from the non-challenge test pack 40 and the outer tube 18 is compressed, breaking the inner tube 18 and releasing the substrate so that it may contact the enzyme on carrier strip 16. The indicator 10 is then incubated for a period of time sufficient for the substrate to react with any active enzyme and form a detectable enzyme-modified product. The enzyme-modified product may be detectable as a signal such as fluorescence, luminescence or a color change. The appearance of a detectable enzyme-modified product is an indication that the sterilization procedure has failed, in that it may not have killed contaminating microorganisms present in the sterilization chamber.

Both the tray 42 and the lid 50 of the non-challenge test pack 40 are preferably made of plastic materials that are thermally-resistant and that do not retain residual sterilant following a sterilization procedure. As used herein, the term "thermally resistant" means capable of withstanding the maximum temperature achieved in a particular sterilization procedure without deformation, shrinkage, melting or decomposition. The maximum temperature achieved during a sterilization procedure varies depending on the type of sterilization procedure that is being used. For example, many steam sterilization procedures are carried out at temperatures of 121° C. or higher, whereas hydrogen peroxide plasma sterilization procedures are commonly performed at temperatures of less than 60° C. In selecting the proper thermally-resistant plastic for use in a tray, these temperature differences between the various sterilization procedures must properly be taken into consideration and a plastic should be selected with a glass transition temperature above the maximum temperature of the sterilization procedure in which the indicator will be used.

In a preferred embodiment of the non-challenge test pack, suitable for use in hydrogen peroxide plasma sterilization procedures, the tray is made of polyethylene terephthalate with a glycol additive (PETG). Other examples of suitable thermally-resistant plastics for used in test pack tray 42 include polyvinyl chloride, polyethylene, ultra-high molecular weight polyethylene, polyetheramide, polysulfones, chorotrifluoroethylene, polyvinylfluoride, polytetrafluoroethylene (PTFE), polypropylene, polystyrene, and polyesters.

The lid 50 may be made of the same material as the tray 42. Preferably the lid 20 is made of a plastic material that is translucent or transparent. In the most preferred embodiment, suitable for use in hydrogen peroxide plasma sterilization procedures, the lid 50 is made of a transparent film and is heat sealed to the rim surface 44. An example of a suitable transparent film is a polyester film coated with a blend of polyethylene and ethylene vinylacetate, commercially available as SCOTCHPAK™ Polyester Film from 3M Company, St. Paul, Minn.

Figure 9:
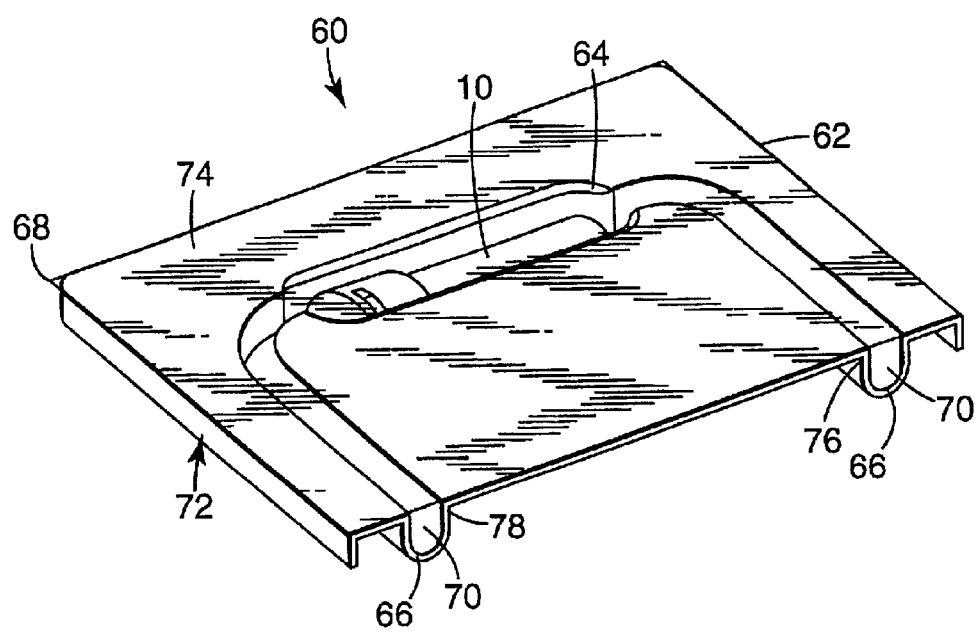
FIG. 9 is a perspective view of a preferred embodiment of the lumen-challenge test pack of the invention.

FIG. 9 shows an alternative test pack, referred to herein as a lumen-challenge test pack, which provides additional resistance to a sterilization indicator that is equivalent to the resistance the indicator would experience if placed within a lumen having a defined cross-sectional area and length. Lumen-challenge test packs provide an accurate method of determining whether a sterilization procedure would be effective in killing microorganisms that may be located deep within the interior of a tube-like instrument.

The lumen-challenge test pack 60 includes a tray 72 for holding a sterilization indicator 10 and a lid 68. The tray 72 is made of thermally-resistant plastic and has a substantially planar surface 74 having an edge 62 that defines the perimeter of the tray 72. A trough 64 for holding a sterilization indicator 10 is recessed into the planar surface 74. A groove 66 having a defined length is recessed into the planar surface forming a continuous path that extends through the recessed trough 64 and penetrates the edge 62 at two points 76, 78. The lid 68 forms a seal with the substantially planar surface 74 that is substantially impermeable to sterilant. The seal may be formed by placing a layer of adhesive between the planar surface 74 and the surface of the lid 68 that are in contact with each other, or by heat sealing. The space between the lid 68 and the groove 66 defines a lumen path 70 through which sterilant is conducted from the sterilization chamber to the sterilization indicator 10.

Figure 10:
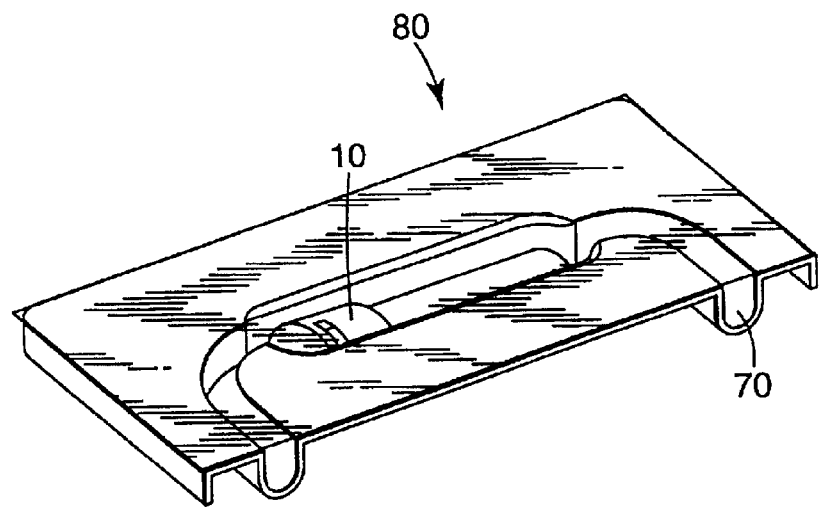
FIG. 10 is a perspective view of an alternative preferred embodiment of the test pack of the invention.

The lumen path 70 has a defined length and cross-sectional area. The dimensions of the lumen path may be selected or adjusted to duplicate the conditions in a lumen having known dimensions. In a preferred embodiment of the test pack, which may preferably be used to test the effectiveness of a hydrogen peroxide plasma sterilization procedure, the lumen path is about approximately twelve inches (30.48 cm) long and has a cross-sectional area that is about the area of a circle having a diameter of 0.25 inches (0.635 cm). However, any lumen length and cross-sectional area may be chosen, and all are considered to be within the scope of the invention. FIG. 10, for example, shows an alternative embodiment of the lumen-challenge test pack 80 in which the lumen path has a different length than the lumen path 70 shown in FIG. 8.

In use the test pack 60 is placed in a sterilization chamber and exposed to a sterilization procedure, during which sterilant travels along the lumen path 76 and contacts the sterilization indicator 10. At the end of the procedure, the sterilization indicator 10 is removed from the test pack and handled as described above with reference to the non-challenge test pack.

The tray 72 and the lid 68 are made of thermally-resistant plastic materials that should be selected in the manner described above with regard to the non-challenge test pack. In a preferred embodiment suitable for use in hydrogen peroxide plasma procedures, the tray 72 is made of polyethylene terephthalate with a glycol additive (PETG) and the lid is made of a transparent film comprising a blend of polyethylene and ethylene vinylacetate, commercially available as SCOTCHPAK™ Polyester Film from 3M Company, St. Paul, Minn. The film 68 may be heat-sealed to the tray 72.

The operation of the present invention will be further described with regard to the following detailed examples. These examples are offered to further illustrate the various specific and preferred embodiments and techniques. It should be understood, however, that many variations and modifications may be made while remaining within the scope of the present invention.

EXAMPLES

Examples 1–5 report the results of tests to determine whether sterilization indicators prepared with spores that have been treated with the chemicals listed in Tables 1–5 demonstrate increased resistance to premature inactivation of enzyme in prevacuum steam sterilization cycles. Examples 6–9 report the results of tests to determine whether sterilization indicators prepared with spores that have been treated with the chemicals listed in Tables 6–9 demonstrate increased resistance to premature inactivation of enzyme in hydrogen peroxide plasma sterilization procedures. Example 10 reports the results of tests that demonstrate the effectiveness of the non-challenge test pack and the lumen-challenge test pack of the invention.

Preparation of Indicators

Sterilization indicators for Examples 1–5 were constructed as illustrated in FIGS. 1 and 2, according to the methods set forth in U.S. Pat. No. 5,252,484. The indicators prepared for the Examples were dual rapid readout indicators that provided both a rapid, enzyme-based efficacy test and a confirmatory spore outgrowth test. Spores coated on the carrier strip 16 served as the source of active enzyme whose activity was measured by the rapid enzyme test. These same spores were then incubated in the spore outgrowth portion of the test.

*Bacillus stearothermophilus*, commercially available as ATCC 7953 from American Type Culture Collection, Rockville, Md., was grown overnight (16 hours) at 58° C. in tryptic soy broth. This culture was used to inoculate the surface of agar plates consisting of 8 g/l nutrient broth, 4 g/l yeast extract, 0.1 g/l manganese chloride and 20 g/l agar at pH 7.2. Plates were incubated at 58° C. for 72 hours. Spores were scraped from the plates and suspended in sterile distilled water. The spores were separated from the vegetative debris by centrifuging the suspension at 7000 rpm and 4° C. for 20 minutes. The supernatant was poured off and the spores were resuspended in sterile distilled water. The cleaning procedure was repeated several times. After the final wash, the spores were suspended in sterile distilled water, at a concentration of approximately $1 \times 10^8$ spores per milliliter.

The spores were then treated with the chemicals identified in Tables 1–5. All chemicals tested were obtained from commercial sources. The spores were centrifuged at 6000 rpm for 10 minutes. The supernatant was removed and mixed with coating chemicals at the concentrations indicated in the tables. The supernatant and coating chemical mixtures were heated at 60–80° C. for several minutes and vortexed to get the material into solution. The spores were then mixed into the sterilant-resistant chemical solution. The sterilant-resistant chemical solution was applied to 5×25 mm, 591 A paper strips (Schleicher & Schuell, Inc., Keene, N. H.) by pipetting 10–15 microliters to each strip for a final population of about $1 \times 10^6$ spores per strip. The strips were dried 16 hours at 37° C.

The treated spore strips were placed on the bottom of the outer container 12 of the indicator 10 and a barrier was inserted between the spore strip 16 and the inner container 18, which contained enzyme substrate. A 1.75 mm (11/16 inch) disc of polypropylene blown microfiber material, with a weight of 200 g/m², commercially available as "THIN-SULATE™ 200-B brand Thermal Insulation" from 3M Company, St. Paul, Minn., was used as the barrier. The inner container 18 contained 0.67 ml nutrient medium, consisting of 17 g of a bacteriological peptone and a 0.17 g/l of L-alanine, as well as 0.1 g 4-methylumbelliferyl-alpha-D-glucoside, commercially available from Sigma Chemical Company, St. Louis, Mo., dissolved in 200 microliters of N,N-dimethylformamide, and 0.03 g bromocresol purple pH indicator dye, per liter of water. The pH of the enzyme substrate and nutrient medium solution was adjusted to 7.6 with 0.1N sodium hydroxide.

The outer vial 12 and the cap 26 are both made of polypropylene. The outer vial 12 was 5.08 cm (2.0 inches) long, with an outer diameter of 85.1 mm (0.335 inches) and an internal diameter of 77.0 mm (0.303 inches). The cap 26 was 1.275 cm (0.510 inches) long with an internal diameter of 83.3 mm (0.328 inches). The inner container 18 was made of glass and was 3.96 cm (1.56 inches) long, with an outer diameter of 65.5 mm (0.258 inches) and a wall thickness of 2.5 mm (0.010 inches). The closure member 22 was a 1.27 mm (0.5 inches) in diameter piece of sterilization grade filter paper.

Sterilization indicators for Examples 6–9 were prepared as described above with the exception that closure member 22 of the sterilization indicator was constructed of TYVEK™ high-density polyethylene fiber material, commercially available from E. I. du Pont de Nemours and Co., Wilmington, Del.

Example 1

This example provides that sterilization indicators made with spores that have been treated with the chemicals in Table 1 demonstrate improved accuracy when compared to indicators made with untreated spores. The chemicals in Table 1 are polyglycerol alkyl esters or ethoxylated glycerol esters.

Sterilization indicators were made as described above with each of the chemicals and concentrations described in Table 1. Control indicators were made using untreated spores. The indicators were placed in metal instrument trays and exposed at 121° C. in a Getinge Steam Sterilizer (Getinge International, Inc., 1100 Towbin Ave., Lakewood, N.J.) using a 4-pulse prevacuum cycle at 121° C. with a vacuum level of 0.075–0.085 bar and a steam pulse to 1.00 bar for each pulse. Indicators were exposed in the sterilizer for between 7 and 13 minutes. This cycle is depicted in the time-pressure diagram in FIG. 5. After exposure the inner containers containing the enzyme substrate and nutrient medium were crushed and the indicators were incubated at 60° C. The indicators were examined for fluorescence using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation at 60° C.

The chemicals tested were obtained from commercial sources. Decaglycerol monostearate, hexaglyceryl monostearate and tetraglyceryl monostearate were obtained from Nikko Chemicals Co., Tokyo, Japan. Glycereth-7-diisononanoate was obtained from Alzo Co. of Matawan, N.J.

The number of growth positive indicators detected after 168 hours of incubation is recorded in Table 1. The percentages of these growth positive indicators that also demonstrated fluorescence at 1 hr, 2 hr, 3 hr, 4 hr, 5 hr and 6 hr are also recorded in Table 1. For purposes of judging the accuracy of the sterilization indicators in Table 1, a fluorescent positive percentage of 100% is perfect, indicating that all the growth positives were detected as fluorescent positives and no false negatives were detected. A fluorescent positive number of less than 100%, on the other hand, indicates that there were one or more false negatives, in that some of the indicators that were negative for fluorescence were later detected as positive for spore growth.

TABLE 1

| COATING CHEMICAL | CONCEN-TRATION mg/ml. | TOTAL TESTED[1] | NO. GROWTH POSITIVE 168 HR | FLUORESCENCE - PERCENT POSITIVE | | | | | |
|---|---|---|---|---|---|---|---|---|---|
| | | | | 1 HR | 2 HR | 3 HR | 4 HR | 5 HR | 6 HR |
| Untreated Control | — | 113 | 44 | 0 | 9.1 | 38.6 | 61.4 | 70.5 | 79.5 |
| Decaglyceryl Monostearate | 10 | 96 | 39 | 0 | 41.0 | 74.4 | 82.1 | 87.2 | 89.7 |

TABLE 1-continued

| COATING CHEMICAL | CONCEN-TRATION mg/ml. | TOTAL TESTED[1] | NO. GROWTH POSITIVE 168 HR | FLUORESCENCE - PERCENT POSITIVE | | | | | |
|---|---|---|---|---|---|---|---|---|---|
| | | | | 1 HR | 2 HR | 3 HR | 4 HR | 5 HR | 6 HR |
| Decaglyceryl Monostearate | 20 | 96 | 34 | 0 | 17.6 | 73.5 | 91.2 | 100 | 100 |
| Decaglyceryl Monostearate | 40 | 114 | 59 | 0 | 69.5 | 91.5 | 100 | 100 | 100 |
| Decaglyceryl Monostearate | 80 | 96 | 55 | 0 | 85.5 | 96.4 | 100 | 100 | 100 |
| Decaglyceryl Monostearate | 100 | 72 | 34 | 8.8 | 85.3 | 100 | 100 | 100 | 100 |
| Hexaglyceryl Monostearate | 5 | 112 | 50 | 0 | 32.0 | 78.0 | 84.0 | 90.0 | 94.0 |
| Hexaglyceryl Monostearate | 10 | 96 | 44 | 0 | 31.8 | 63.6 | 79.5 | 84.1 | 86.4 |
| Hexaglyceryl Monostearate | 20 | 96 | 44 | 0 | 61.4 | 86.4 | 95.5 | 97.7 | 97.7 |
| Tetraglyceryl Monostearate | 5 | 72 | 37 | 0 | 43.2 | 67.6 | 83.8 | 94.6 | 97.3 |
| Tetraglyceryl Monostearate | 10 | 54 | 54 | 0 | 63.0 | 81.5 | 94.4 | 96.3 | 98.1 |
| Tetraglyceryl Monostearate | 20 | 96 | 70 | 0 | 74.3 | 92.9 | 100.0 | 100.0 | 100.0 |
| Tetraglyceryl Monostearate | 40 | 24 | 19 | 0 | 94.7 | 100.0 | 100.0 | 100.0 | 100.0 |
| Glycereth-7-diisononanoate | 20 | 24 | 6 | 0 | 0 | 66.7 | 83.3 | 83.3 | 83.3 |
| Glycereth-7-diisononanoate | 40 | 42 | 17 | 0 | 64.7 | 88.2 | 88.2 | 94.1 | 100.0 |

[1]Total number of indicators exposed to the sterilization procedure regardless of the period of time of the exposure.

Example 2

This example provides evidence of the effect that treating spores with polyglycerol compounds without alkyl esters or ethers has on the accuracy of sterilization indicators made with the treated spores when compared to indicators made with untreated spores.

Sterilization indicators were made as described above with each of the chemicals and concentrations described in Table 2. Control indicators were made using untreated spores. The indicators were placed in metal instrument trays and exposed at 121° C. in a Getinge Steam Sterilizer (Getinge International, Inc., 1100 Towbin Ave., Lakewood, N.J.) using a 4-pulse prevacuum cycle at 121° C. with a vacuum level of 0.075–0.085 bar and a steam pulse to 1.00 bar for each pulse. Indicators were exposed in the sterilizer for between 7 and 13 minutes. This cycle is depicted in the time-pressure diagram in FIG. 5. After exposure the inner containers containing the enzyme substrate and nutrient medium were crushed and the indicators were incubated at 60° C. The indicators were examined for fluorescence using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation at 60° C.

The number of growth positive indicators detected after 168 hours of incubation is recorded in Table 2. The percentages of these growth positive indicators that demonstrated fluorescence at 1 hr, 2 hr, 3 hr, 4 hr, 5 hr and 6 hr are also recorded in Table 2. For purposes of judging the accuracy of the sterilization indicators in Table 2, a fluorescent positive percentage of 100% is perfect, indicating that all the growth positives were detected. A fluorescent positive number of less than 100%, on the other hand, indicates that there were one or more false negatives, in that some of the indicators that were negative for fluorescence were later detected as positive for spore growth.

When used as spore coatings, hexaglycerol and triglycerol did not improve the accuracy of sterility indicators.

The chemicals tested were obtained from commercial sources. Decaglycerol, hexaglycerol and triglycerol were obtained from Lonza, Inc., Fairlawn, N.J.

TABLE 2

| COATING CHEMICAL | CONCEN-TRATION mg/ml. | TOTAL TESTED[2] | NO. GROWTH POSITIVE 168 HR | FLUORESCENCE - PERCENT POSITIVE | | | | | |
|---|---|---|---|---|---|---|---|---|---|
| | | | | 1 HR | 2 HR | 3 HR | 4 HR | 5 HR | 6 HR |
| Untreated Control | — | 113 | 44 | 0 | 9.1 | 38.6 | 61.4 | 70.5 | 79.5 |
| Decaglycerol | 5 | 48 | 13 | 0 | 0 | 0 | 23.1 | 23.1 | 30.8 |
| Decaglycerol | 10 | 46 | 13 | 0 | 0 | 7.7 | 23.1 | 23.1 | 30.8 |
| Decaglycerol | 20 | 47 | 11 | 0 | 0 | 9.1 | 18.2 | 45.5 | 63.6 |

TABLE 2-continued

| COATING CHEMICAL | CONCEN-TRATION mg/ml. | TOTAL TESTED[2] | NO. GROWTH POSITIVE 168 HR | FLUORESCENCE - PERCENT POSITIVE | | | | | |
|---|---|---|---|---|---|---|---|---|---|
| | | | | 1 HR | 2 HR | 3 HR | 4 HR | 5 HR | 6 HR |
| Decaglycerol | 40 | 48 | 26 | 0 | 0 | 7.7 | 42.3 | 46.2 | 53.8 |
| Decaglycerol | 80 | 48 | 25 | 0 | 12.0 | 36.0 | 64.0 | 72.0 | 76.0 |
| Decaglycerol | 100 | 48 | 29 | 0 | 6.9 | 48.3 | 69.0 | 79.3 | 89.7 |
| Hexaglycerol | 5 | 46 | 11 | 0 | 0 | 0 | 9.1 | 45.5 | 63.6 |
| Hexaglycerol | 10 | 48 | 20 | 0 | 0 | 5.0 | 15.0 | 35.0 | 50.0 |
| Hexaglycerol | 20 | 48 | 18 | 0 | 0 | 11.1 | 38.9 | 50.0 | 61.1 |
| Hexaglycerol | 40 | 45 | 26 | 0 | 0 | 26.9 | 46.2 | 53.8 | 61.5 |
| Hexaglycerol | 80 | 48 | 24 | 0 | 0 | 37.5 | 58.3 | 70.8 | 70.8 |
| Triglycerol | 5 | 46 | 10 | 0 | 0 | 0 | 10.0 | 30.0 | 40.0 |
| Triglycerol | 10 | 47 | 15 | 0 | 6.7 | 20.0 | 26.7 | 53.3 | 60.0 |
| Triglycerol | 20 | 48 | 24 | 0 | 0 | 8.3 | 29.2 | 41.7 | 45.8 |
| Triglycerol | 40 | 48 | 27 | 0 | 0 | 29.6 | 48.1 | 51.9 | 63.0 |
| Triglycerol | 80 | 48 | 31 | 0 | 3.2 | 38.7 | 51.6 | 58.1 | 64.5 |

[2]Total number of indicators exposed to the sterilization procedure regardless of the period of time of the exposure.

Example 3

This example provides evidence that sterilization indicators made with spores that have been treated with a mixture of decaglyceryl monostearate and sorbitol, or with decaglycerol monostearate alone, demonstrate improved accuracy when compared with sterility indicators made with untreated spores or spores treated with sorbitol alone.

Sterilization indicators were made as described above with each of the chemicals and concentrations described in Table 3. Control indicators were made using untreated spores. The indicators were placed in metal instrument trays and exposed at 121° C. in a Getinge Steam Sterilizer (Getinge International, Inc., 1100 Towbin Ave., Lakewood, N.J.) using a 4-pulse prevacuum cycle at 121° C. with a vacuum level of 0.075–0.085 bar and a steam pulse to 1.00 bar for each pulse. Indicators were exposed in the sterilizer for between 7 and 15 minutes. This cycle is depicted in the time-pressure diagram in FIG. 5. After exposure the inner containers containing the enzyme substrate and nutrient medium were crushed and the indicators were incubated at 60° C. The indicators were examined for fluorescence using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation at 60° C.

The number of growth positive indicators detected after 168 hours of incubation is recorded in Table 3. The percentages of these growth positive indicators that demonstrated fluorescence at 1 hr, 2 hr, 3 hr and 4 hr are recorded in Table 3. For purposes of judging the accuracy of the sterilization indicators in Table 2, a fluorescent positive percentage of 100% is perfect, indicating that all the growth positives were detected. A fluorescent positive number of less than 100%, on the other hand, indicates that there were one or more false negatives, in that some of the indicators that were negative for fluorescence were later detected as positive for spore growth.

The chemicals tested were obtained from commercial sources. Sorbitol was obtained from Paddock Laboratories, Minneapolis, Minn. Decaglyceryl monostearate was obtained from Nikko Chemicals, Co., Tokyo, Japan.

TABLE 3

| COATING CHEMICAL | CONCEN-TRATION mg/ml. | TOTAL TESTED[3] | GROWTH POSITIVE 168 HR | FLUORESCENCE - PERCENT POSITIVE | | | |
|---|---|---|---|---|---|---|---|
| | | | | 1 HR | 2 HR | 3 HR | 4 HR |
| Uncoated Control | — | 48 | 20 | 0 | 15.0 | 55.0 | 85.0 |
| Sorbitol | 100 | 48 | 36 | 0 | 52.8 | 83.3 | 91.7 |
| Decaglycerol Monostearate | 100 | 48 | 20 | 0 | 100.0 | 100.0 | 100.0 |
| Mixture of a) Decaglycerol Monostearate and b) Sorbitol | a) 100 b) 100 | 48 | 27 | 40.7 | 100.0 | 100.0 | 100.0 |

[3]Total number of indicators exposed to the sterilization procedure regardless of the period of time of the exposure.

Example 4

This example provides evidence that some of the chemicals in Table 4, when used to treat spores used in sterilization indicators, improve the accuracy of the indicators when compared to indicators made with untreated spores.

Sterilization indicators were made as described above with each of the chemicals and concentrations described in Table 4. Control indicators were made using untreated spores. The indicators were placed in metal instrument trays and exposed at 121° C. in a Getinge Steam Sterilizer (Getinge International, Inc., 1100 Towbin Ave., Lakewood, N.J.) using a 4-pulse prevacuum cycle at 121° C. with a vacuum level of 0.075–0.085 bar and a steam pulse to 1.00 bar for each pulse. Indicators were exposed in the sterilizer for between 7 and 18 minutes. This cycle is depicted in the time-pressure diagram in FIG. 5. After exposure the inner containers containing the enzyme substrate and nutrient medium were crushed and the indicators were incubated at 60° C. The indicators were examined for fluorescence using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation at 60° C.

The number of growth positive indicators detected after 168 hours of incubation is recorded in Table 4. The percentages of these growth positive indicators that demonstrated fluorescence at 1 hr, 2 hr, 3 hr and 4 hr are recorded in Table 4. For purposes of judging the accuracy of the sterilization indicators in Table 4, a fluorescent positive percentage of 100% is perfect, indicating that all the growth positives were detected. A fluorescent positive number of less than 100%, on the other hand, indicates that there were one or more false negatives, in that some of the indicators that were negative for fluorescence were later detected as positive for spore growth.

The accuracy of sterilization indicators was improved when spores used in the indicators were treated with decaglyceryl monostearate, decaglyceryl monolaurate, hexaglyceryl monolaurate, tetraglyceryl monooleate, decaglyceryl monooleate, decaglycerol dipalmitate and hexaglyceryl distearate. This effect was increased when the spores were treated with the chemicals at higher concentrations.

The chemicals tested were obtained from commercial sources. Decaglycerol monostearate, hexaglyceryl polyricinolate, hexaglyceryl pentaoleate, decaglyceryl monolaurate, hexaglyceryl monolaurate, tetraglyceryl monooleate, and decaglyceryl trioleate were obtained from Nikko Chemicals Co., Tokyo, Japan. Decaglyceryl monooleate, decaglyceryl dipalmitate, hexaglyceryl dioleate, decaglyceryl hexaoleate, hexaglyceryl distearate and decaglyceryl decaoleate were obtained from Lonza, Inc., Fairlawn, N.J.

TABLE 4

| COATING CHEMICAL | CONCEN-TRATION mg/ml | TOTAL TESTED[4] | NO. GROWTH POSITIVE 168 HR | FLUORESCENCE - PERCENT POSITIVE | | | |
|---|---|---|---|---|---|---|---|
| | | | | 1 HR | 2 HR | 3 HR | 4 HR |
| Untreated Control | — | 42 | 29 | 20.7 | 31.0 | 44.8 | 58.6 |
| Untreated Control | — | 42 | 30 | 0 | 26.7 | 43.3 | 66.7 |
| Sorbitol | 100 | 42 | 37 | 5.4 | 40.5 | 81.1 | 89.2 |
| Decaglyceryl Monostearate | 50 | 42 | 29 | 13.8 | 86.2 | 100.0 | 100.0 |
| Hexaglyceryl Polyricinolate | 50 | 42 | 23 | 0 | 13.0 | 52.2 | 56.5 |
| Hexaglyceryl Polyricinolate | 100 | 45 | 31 | 9.7 | 19.4 | 32.3 | 45.2 |
| Decaglyceryl Pentaoleate | 50 | 42 | 16 | 0 | 0 | 18.8 | 31.3 |
| Decaglyceryl Pentaoleate | 100 | 47 | 24 | 12.5 | 25.0 | 37.5 | 45.8 |
| Decaglyceryl Monolaurate | 50 | 42 | 11 | 0 | 27.3 | 72.7 | 72.7 |
| Decaglyceryl Monolaurate | 100 | 45 | 23 | 87 | 100.0 | 100.0 | 100.0 |
| Hexaglyceryl Monolaurate | 50 | 42 | 7 | 0 | 28.6 | 57.1 | 71.4 |
| Hexaglyceryl Monolaurate | 100 | 43 | 20 | 90.0 | 100.0 | 100.0 | 100.0 |
| Tetraglyceryl Monooleate | 50 | 42 | 17 | 0.0 | 52.9 | 52.9 | 58.8 |
| Tetraglyceryl Monooleate | 100 | 47 | 35 | 57.1 | 100.0 | 100.0 | 100.0 |
| Decaglyceryl Trioleate | 50 | 42 | 19 | 0.0 | 21.1 | 47.4 | 68.4 |
| Decaglyceryl Trioleate | 100 | 47 | 26 | 23.1 | 50.0 | 73.1 | 92.3 |
| Decaglyceryl Monooleate | 50 | 42 | 10 | 0 | 0 | 0 | 0 |
| Decaglyceryl Monooleate | 100 | 47 | 26 | 7.7 | 23.1 | 50 | 73.1 |
| Decaglyceryl Dipalmitate | 50 | 42 | 28 | 7.1 | 67.9 | 89.3 | 92.9 |
| Decaglyceryl Dipalmitate | 100 | 33 | 26 | 34.6 | 61.5 | 69.2 | 69.2 |
| Hexaglyceryl Dioleate | 50 | 42 | 7 | 0 | 0 | 0 | 0 |
| Hexaglyceryl Dioleate | 100 | 47 | 23 | 0 | 0 | 0 | 0 |
| Decaglyceral Hexaoleate | 50 | 42 | 9 | 0 | 0 | 22.2 | 55.6 |
| Decaglyceral Hexaoleate | 100 | 47 | 18 | 5.6 | 16.7 | 27.8 | 33.3 |

TABLE 4-continued

| COATING CHEMICAL | CONCEN-TRATION mg/ml. | TOTAL TESTED[4] | NO. GROWTH POSITIVE 168 HR | FLUORESCENCE - PERCENT POSITIVE | | | |
|---|---|---|---|---|---|---|---|
| | | | | 1 HR | 2 HR | 3 HR | 4 HR |
| Hexaglyceryl Distearate | 25 | 30 | 29 | 27.6 | 51.7 | 58.6 | 62.1 |
| Hexaglyceryl Distearate | 50 | 33 | 33 | 30.3 | 57.6 | 97 | 100 |
| Hexaglyceryl Distearate | 100 | 21 | 21 | 71.4 | 100 | 100 | 100 |
| Decaglyceryl Decaoleate | 50 | 42 | 31 | 0 | 19.4 | 29.0 | 41.9 |
| Decaglyceryl Decaoleate | 100 | 46 | 30 | 16.7 | 20 | 30 | 50 |

[4]Total number of indicators exposed to the sterilization procedure regardless of the period of time of the exposure.

Example 5

This example provides evidence that some of the chemicals in Table 5, when used to treat spores used in sterilization indicators, improved the accuracy of the indicators when compared to indicators made with untreated spores.

Sterilization indicators were made as described above with each of the chemicals and concentrations described in Table 5. Control indicators were made using untreated spores. The indicators were placed in metal instrument trays and exposed at 121° C. in a Getinge Steam Sterilizer (Getinge International, Inc., 1100 Towbin Ave., Lakewood, N.J.) using a 4-pulse prevacuum cycle at 121° C. with a vacuum level of 0.075–0.085 bar and a steam pulse to 1.00 bar for each pulse. Indicators were exposed in the sterilizer for between 7 and 13 minutes. This cycle is depicted in the time-pressure diagram in FIG. 5. After exposure the inner containers containing the enzyme substrate and nutrient medium were crushed and the indicators were incubated at 60° C. The indicators were examined for fluorescence using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation at 60° C.

The number of growth positive indicators detected after 168 hours of incubation is recorded in Table 5. The percentages of these growth positive indicators that demonstrated fluorescence at 1 hr, 2 hr, 3 hr and 4 hr are also recorded in Table 5. For purposes of judging the accuracy of the sterilization indicators in Table 5, a fluorescent positive percentage of 100% is perfect, indicating that all the growth positives were detected. A fluorescent positive number of less than 100%, on the other hand, indicates that there were one or more false negatives, in that some of the indicators that were negative for fluorescence were later detected as positive for spore growth.

The accuracy of sterilization indicators was improved when spores used in the indicators were treated with polyoxyethylene (5) glyceryl monostearate, decaglyceryl monooleate, and decaglyceryl monomyristate, decaglyceryl monoisostearate and decaglyceryl diisostearate. This effect was increased when the spores were treated with the chemicals at higher concentrations.

All chemicals were obtained from Nikko Chemicals Co., Tokyo, Japan.

TABLE 5

| COATING CHEMICAL | CONCEN-TRATION mg/ml. | TOTAL TESTED[5] | NO. GROWTH POSITIVE 168 HR | FLUORESCENCE - PERCENT POSITIVE | | | |
|---|---|---|---|---|---|---|---|
| | | | | 1 HR | 2 HR | 3 HR | 4 HR |
| Control | — | 9 | 7 | 28.6 | 42.9 | 42.9 | 42.9 |
| POE[6] (5) Glyceryl Monostearate | 50 | 25 | 15 | 0 | 100.0 | 100.0 | 100.0 |
| POE (5) Glyceryl Monostearate | 100 | 12 | 5 | 0 | 100 | 100 | 100 |
| POE (60) Sorbitol Tetrastearate | 50 | 9 | 5 | 0 | 0 | 0 | 0 |
| POE (15) Glyceryl Monostearate | 50 | 15 | 7 | 0 | 0 | 42.9 | 57.1 |
| POE (15) Glyceryl Monostearate | 100 | 15 | 4 | 0 | 0 | 0 | 0 |
| POE (10) Phytosterol | 50 | 9 | 2 | 0 | 0 | 0 | 0 |
| Decaglyceryl Monooleate | 50 | 27 | 6 | 0 | 0 | 0 | 0 |
| Decaglyceryl Monooleate | 100 | 27 | 2 | 0 | 50 | 100 | 100 |
| Sodium POE (8) Oleyl Ether Phosphate | 50 | 9 | 6 | 0 | 0 | 0 | 0 |

TABLE 5-continued

| COATING CHEMICAL | CONCEN- TRATION mg/ml. | TOTAL TESTED[5] | NO. GROWTH POSITIVE 168 HR | FLUORESCENCE - PERCENT POSITIVE | | | |
|---|---|---|---|---|---|---|---|
| | | | | 1 HR | 2 HR | 3 HR | 4 HR |
| Sodium POE (8) Oleyl Ether Phosphate | 100 | 9 | 3 | 0 | 0 | 0 | 0 |
| POE (20) Sorbitan Monostearate | 50 | 9 | 5 | 0 | 0 | 0 | 0 |
| POE (20) Sorbitan Monostearate | 100 | 9 | 2 | 0 | 0 | 0 | 0 |
| Decaglyceryl Monomyristate | 50 | 9 | 3 | 0 | 33.3 | 33.3 | 33.3 |
| Decaglyceryl Monomyristrate | 100 | 9 | 2 | 0 | 100 | 100 | 100 |
| Decaglyceryl Monoisostearate | 50 | 19 | 9 | 33.3 | 77.8 | 88.9 | 88.9 |
| Decaglyceryl Monoisostearate | 100 | 15 | 8 | 37.5 | 100 | 100 | 100 |
| Decaglyceryl Diisostearate | 50 | 14 | 10 | 30 | 80.0 | 100 | 100 |
| Decaglyceryl Diisostearate | 100 | 22 | 14 | 28.6 | 100.0 | 100 | 100 |
| POE (15) Glyceryl Monooleate | 50 | 9 | 1 | 0 | 0 | 0 | 0 |
| POE (5) Glyceryl Monooleate | 50 | 9 | 2 | 0 | 0 | 0 | 0 |
| POE (5) Glyceryl Monooleate | 100 | 9 | 2 | 0 | 0 | 0 | 0 |
| POE (60) Sorbitol Tetraoleate | 50 | 9 | 2 | 0 | 0 | 0 | 0 |
| POE (60) Sorbitol Tetraoleate | 100 | 9 | 2 | 0 | 0 | 0 | 0 |

[5]Total tested is the total number of indicators exposed to the sterilization procedure regardless of the period of time of the exposure.
[6]Polyoxyethylene Example 6

This Example reports the results of an experiment to determine whether enzymes associated with spores that have been treated with the chemicals listed in Table 6 are more resistant to premature inactivation in hydrogen peroxide plasma sterilization procedures than enzymes associated with untreated spores.

Sterilization indicators were made as described above with spores that had been coated with each of the chemicals and concentrations listed in Table 6. The indicators were placed in instrument trays and exposed to a hydrogen peroxide plasma sterilization procedure at 45–55° C. in a STERRAD™ 100SI GMP Sterilizer, obtained from Advanced Sterilization Products Co., Irvine, Calif. During the sterilization procedure a vacuum was drawn in the sterilization chamber for 5–6 minutes until the pressure was reduced to 300 mTorr. A 1.8 ml aliquot of an aqueous solution of 58–60% hydrogen peroxide was then injected into the sterilization chamber over a period of about 6 minutes, yielding an empty chamber concentration of 6–7 mg/ml hydrogen peroxide, and hydrogen peroxide vapor was allowed to diffuse throughout the chamber for 1–22 minutes at 6–10 Torr. A vacuum was then drawn, reducing the pressure to 500 mTorr and removing all detectable hydrogen peroxide vapor from the chamber. A plasma phase was then generated in the chamber by emitting an RF power source at 400 watts and 13.56 MHz for about 15–16 minutes at 500 mTorr, after which the chamber was vented for 3–4 minutes until atmospheric pressure was reached in the chamber.

After exposure to the sterilization procedure, the indicators were removed from the sterilizer and the inner containers containing the enzyme substrate and nutrient medium were crushed. The indicators were then incubated at 60° C. and examined for fluorescence every hour for 5 hours using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation.

The number of growth positive indicators detected after 168 hours of incubation is recorded in Table 6. The percentages of these growth positive indicators that demonstrated fluorescence at 1 hr, 2 hr, 3 hr, 4 hr and 5 hr are also recorded in Table 6. For purposes of judging the accuracy of the sterilization indicators in Table 6, a fluorescent positive percentage of 100% is perfect, indicating that all growth positives were detected. A fluorescent positive number of less than 100%, on the other hand, indicates that there were one or more false negatives, in that some of the indicators that were negative for fluorescence were later detected as positive for spore growth.

The data in Table 6 indicates that the accuracy of the sterilization indicators is improved in hydrogen peroxide plasma sterilization procedures, 1–3 hours after exposure, compared to indicators made with untreated spores, when the indicators are prepared with spores that have been treated with decaglyceryl decaoleate, decaglycerol pentaoleate, tetraglycerol monooleate, decaglycerol hexaoleate, and 1,2,3-Propantrial. It can be inferred from the data that treatment with these chemicals increases the resistance of the enzyme to premature inactivation in hydrogen peroxide plasma sterilization procedures.

All chemicals listed in Table 6 were obtained from commercial sources. Decaglyceryl decaoleate, decaglycerol hexaoleate, hexaglycerol dioleate and decaglycerol pentaoleate were obtained from Lonza, Inc., Fairlawn, N.J. Tetraglycerol monooleate and decaglycerol trioleate were obtained from Nikko Chemicals Co., Tokyo, Japan.

were crushed. The indicators were then incubated at 60° C. and examined for fluorescence every hour for 5 hours using a 3M™ ATTEST™ Model 190 Rapid Autoreader, commercially available from 3M Company, St. Paul, Minn.

TABLE 6

| COATING CHEMICAL | CONCENTRATION mg/ml | TOTAL TESTED[7] | NO. GROWTH POSITIVE 168 HR. | FLUORESCENCE - PERCENT POSITIVE | | | | |
|---|---|---|---|---|---|---|---|---|
| | | | | 1 HR. | 2 HR. | 3 HR. | 4 HR. | 5 HR. |
| Untreated Control | — | 110 | 75 | 73.3 | 84.0 | 94.7 | 100 | 100 |
| Decaglyceryl Decaoleate | 10 | 100 | 49 | 83.7 | 100 | 100 | 100 | 100 |
| Decaglycerol Pentaoleate | 50 | 30 | 17 | 82.4 | 94.1 | 100 | 100 | 100 |
| Tetraglycerol Monooleate | 50 | 14 | 11 | 76.6 | 90.9 | 100 | 100 | 100 |
| Decaglycerol Trioleate | 50 | 53 | 40 | 85.0 | 97.5 | 100 | 100 | 100 |
| Decaglycerol Hexaoleate | 10 | 25 | 12 | 100 | 100 | 100 | 100 | 100 |
| Hexaglycerol Dioleate | 50 | 12 | 6 | 66.7 | 100 | 100 | 100 | 100 |

[7]Total Tested = Total number of indicators exposed to the sterilization procedure.

Example 7

This Example reports the results of an experiment to determine whether enzymes associated with spores that have been treated with the chemicals listed in Table 7 are more resistant to premature inactivation in hydrogen peroxide plasma sterilization procedures than enzymes associated with untreated spores.

Sterilization indicators were made as described above with spores that had been coated with each of the chemicals and concentrations listed in Table 7. The indicators were placed in instrument trays and exposed to a hydrogen peroxide plasma sterilization procedure at 45–55° C. in a STERRAD™ 100SI GMP Sterilizer, obtained from Advanced Sterilization Products Co., Irvine, Calif. During the sterilization procedure a vacuum was drawn in the sterilization chamber for 5–6 minutes until the pressure was reduced to 300 mTorr. A 1.8 ml aliquot of an aqueous solution of 58–60% hydrogen peroxide was then injected into the sterilization chamber over a period of about 6 minutes, yielding an empty chamber concentration of 6–7 mg/ml hydrogen peroxide, and hydrogen peroxide vapor was allowed to diffuse throughout the chamber for 1–22 minutes at 6–10 Torr. A vacuum was then drawn, reducing the pressure to 500 mTorr and removing all detectable hydrogen peroxide vapor from the chamber. A plasma phase was then generated in the chamber by emitting an RF power source at 400 watts and 13.56 MHz for about 15–16 minutes at 500 mTorr, after which the chamber was vented for 3–4 minutes until atmospheric pressure was reached in the chamber.

After exposure to the sterilization procedure, the indicators were removed from the sterilizer and the inner containers containing the enzyme substrate and nutrient medium Additionally, spore growth, as indicated by a color change from purple to yellow, was determined visually after 168 hours of incubation.

The number of growth positive indicators detected after 168 hours of incubation is recorded in Table 7. The percentages of these growth positive indicators that demonstrated fluorescence at 1 hr, 2 hr, 3 hr, 4 hr and 5 hr are also recorded in Table 7. For purposes of judging the accuracy of the sterilization indicators in Table 7, a fluorescence positive percentage of 100% is perfect, indicating that all growth positives were detected. A fluorescent positive number of less than 100%, on the other hand, indicates that there were one or more false negatives, in that some of the indicators that were negative for fluorescence were later detected as positive for spore growth.

The data in Table 7 indicates that the accuracy of sterilization indicators is improved in hydrogen peroxide plasma sterilization procedures, 2–3 hours after exposure, compared to indicators made with untreated spores, when the indicators are prepared with spores that have been treated with decaglyceryl decaoleate, POE (60) glycerol monostearate and POE (20) sorbitan monostearate. It can be inferred from the data that treatment with these chemicals increases the resistance of the enzyme to premature inactivation in hydrogen peroxide plasma sterilization procedures.

All chemicals listed in Table 7 were obtained from commercial sources. Decaglyceryl decaoleate was obtained from Lonza, Inc., Fairlawn, N.J. Decaglyceryl monostearate, hexaglyceryl polyricinolate, POE (60) glycerol monostearate and POE (20) sorbitan monostearate were obtained from Nikko Chemicals Co., Tokyo, Japan.

TABLE 7

| COATING CHEMICAL | CONCENTRATION mg/ml | TOTAL TESTED[8] | NO. GROWTH POSITIVE 168 HR. | FLUORESCENCE - PERCENT POSITIVE | | | | |
|---|---|---|---|---|---|---|---|---|
| | | | | 1 HR. | 2 HR. | 3 HR. | 4 HR. | 5 HR. |
| Untreated Control | — | 110 | 75 | 73.3 | 84.0 | 94.7 | 100 | 100 |
| Decaglyceryl Decaoleate | 10 | 100 | 49 | 83.7 | 100 | 100 | 100 | 100 |
| Decaglycerol Monostearate | 50 | 68 | 59 | 64.4 | 83.0 | 89.8 | 91.3 | 91.3 |
| Hexaglyceryl Polyricinolate | 50 | 20 | 12 | 83.3 | 91.7 | 91.7 | 91.7 | 91.7 |
| POE[9] (60) Glycerol Monostearate | 50 | 16 | 7 | 100 | 100 | 100 | 100 | 100 |

TABLE 7-continued

| COATING CHEMICAL | CONCENTRATION mg/ml | TOTAL TESTED[8] | NO. GROWTH POSITIVE 168 HR. | FLUORESCENCE - PERCENT POSITIVE | | | | |
|---|---|---|---|---|---|---|---|---|
| | | | | 1 HR. | 2 HR. | 3 HR. | 4 HR. | 5 HR. |
| POE (60) Glycerol Monostearate | 100 | 16 | 7 | 57.1 | 57.1 | 71.4 | 71.4 | 71.4 |
| POE (20) Sorbitan Monostearate | 50 | 16 | 6 | 100 | 100 | 100 | 100 | 100 |
| POE (20) Sorbitan Monostearate | 100 | 16 | 8 | 50 | 50 | 62.5 | 75 | 75 |

[8]Total Tested = Total number of indicators exposed to the sterilization procedure.
[9]POE = Polyoxyethylene

Example 8

This Example reports the results of an experiment to determine whether enzymes associated with spores that have been treated with the chemicals listed in Table 8 are more resistant to premature inactivation in hydrogen peroxide plasma sterilization procedures than enzymes associated with untreated spores.

Sterilization indicators were made as described above with spores that had been coated with each of the chemicals and concentrations listed in Table 8. The indicators were placed in instrument trays and exposed to a hydrogen peroxide plasma sterilization procedure at 45–55° C. in a STERRAD™ 100SI GMP Sterilizer, obtained from Advanced Sterilization Products Co., Irvine, Calif. During the sterilization procedure a vacuum was drawn in the sterilization chamber for 5–6 minutes until the pressure was reduced to 300 mTorr. A 1.8 ml aliquot of an aqueous solution of 58–60% hydrogen peroxide was then injected into the sterilization chamber over a period of about 6 minutes, yielding an empty chamber concentration of 6–7 mg/ml hydrogen peroxide, and hydrogen peroxide vapor was allowed to diffuse throughout the chamber for 1–22 minutes at 6–10 Torr. A vacuum was then drawn, reducing the pressure to 500 mTorr and removing all detectable hydrogen peroxide vapor from the chamber. A plasma phase was then generated in the chamber by emitting an RF power source at 400 watts and 13.56 MHz for about 15–16 minutes at 500 mTorr, after which the chamber was vented for 3–4 minutes until atmospheric pressure was reached in the chamber.

After exposure to the sterilization procedure, the indicators were removed from the sterilizer and the inner containers containing the enzyme substrate and nutrient medium were crushed. The indicators were then incubated at 60° C. and examined for fluorescence every hour for 5 hours using a 3m™ ATTEST™ Model 190 Rapid Autoreader, commercially available from 3M Company, St. Paul, Minn. Additionally, spore growth, as indicated by a color change from purple to yellow, was determined visually after 168 hours of incubation.

The number of growth positive indicators detected after 168 hours of incubation is recorded in Table 8. The percentages of these growth positive indicators that demonstrated fluorescence at 1 hr, 2 hr, 3 hr, 4 hr and 5 hr are also recorded in Table 8. For purposes of judging the accuracy of the sterilization indicators in Table 8, a fluorescence positive percentage of 100% is perfect, indicating that all growth positives were detected. A fluorescent positive number of less than 100%, on the other hand, indicates that there were one or more false negatives, in that some of the indicators that were negative for fluorescence were later detected as positive for spore growth.

The data in Table 8 indicates that the accuracy of sterilization indicators is improved in hydrogen peroxide plasma sterilization procedures, 1–3 hours after exposure, compared to indicators made with untreated spores, when the indicators are prepared with spores that have been treated with hexaglyn di-stearate. It can be inferred from the data that treatment with this chemicals increases the resistance of the enzyme to premature inactivation in hydrogen peroxide plasma sterilization procedures.

All chemicals listed in Table 8 were obtained from commercial sources. Alkyl polyglucoside was obtained from Henkel Co., Hoboken, N.J. Hexaglyn di-stearate and decaglycerol dipalmitate were obtained from Lonza, Inc., Fairlawn, N.J. Sodium POE (8) oleyl ether phosphate was obtained from Nikko Chemicals Co., Tokyo, Japan.

TABLE 8

| COATING CHEMICAL | CONCENTRATION mg/ml | TOTAL TESTED[10] | NO. GROWTH POSITIVE 168 HR. | FLUORESCENCE - PERCENT POSITIVE | | | | |
|---|---|---|---|---|---|---|---|---|
| | | | | 1 HR. | 2 HR. | 3 HR. | 4 HR. | 5 HR. |
| Untreated Control | — | 16 | 7 | 14.3 | 57.1 | 85.7 | 100 | 100 |
| Alkyl Polyglucoside | 20 | 12 | 5 | 0 | 0 | 0 | 0 | 0 |
| Alkyl Polyglucoside | 40 | 12 | 1 | 0 | 0 | 0 | 0 | 0 |
| Sodium POE[11] (8) Oleyl Ether Phosphate | 50 | 16 | 0 | 0 | 0 | 0 | 0 | 0 |
| Sodium POE (8) Oleyl Ether Phosphate | 100 | 16 | 0 | 0 | 0 | 0 | 0 | 0 |
| Hexaglyn Di-Stearate | 25 | 16 | 16 | 100 | 100 | 100 | 100 | 100 |
| Hexaglyn Di-Stearate | 50 | 16 | 16 | 100 | 100 | 100 | 100 | 100 |

TABLE 8-continued

| COATING CHEMICAL | CONCENTRATION mg/ml | TOTAL TESTED[10] | NO. GROWTH POSITIVE 168 HR. | FLUORESCENCE - PERCENT POSITIVE | | | | |
|---|---|---|---|---|---|---|---|---|
| | | | | 1 HR. | 2 HR. | 3 HR. | 4 HR. | 5 HR. |
| Hexaglyn Di-Stearate | 100 | 16 | 16 | 100 | 100 | 100 | 100 | 100 |
| Decaglycerol Dipalmitate | 50 | 28 | 27 | 66.7 | 74.1 | 77.8 | 77.8 | 77.8 |

[10]Total Tested = Total number of indicators exposed to the sterilization procedure.
[11]POE = Polyoxyethylene

Example 9

This Example reports the results of an experiment to determine the effective concentration range of decaglyceryl decaoleate for use in treating spores to prevent premature inactivation enzymes associate with the spores in hydrogen peroxide plasma sterilization procedures than enzymes in untreated spores.

Sterilization indicators were made as described above with spores that had been coated with decaglyceryl decaoleate at each of the concentrations listed in Table 9. The indicators were placed in instrument trays and exposed to a hydrogen peroxide plasma sterilization procedure at 45–55° C. in a STERRAD™ 100SI GMP Sterilizer, obtained from Advanced Sterilization Products Co., Irvine, Calif. During the sterilization procedure a vacuum was drawn in the sterilization chamber for 5–6 minutes until the pressure was reduced to 300 mTorr. A 1.8 ml aliquot of an aqueous solution of 58–60% hydrogen peroxide was then injected into the sterilization chamber over a period of about 6 minutes, yielding an empty chamber concentration of 6–7 mg/ml hydrogen peroxide, and hydrogen peroxide vapor was allowed to diffuse throughout the chamber for 1–22 minutes at 6–10 Torr. A vacuum was then drawn, reducing the pressure to 500 mTorr and removing all detectable hydrogen peroxide vapor from the chamber. A plasma phase was then generated in the chamber by emitting an RF power source at 400 watts and 13.56 MHz for about 15–16 minutes at 500 mTorr, after which the chamber was vented for 3–4 minutes until atmospheric pressure was reached in the chamber.

After exposure to the sterilization procedure, the indicators were removed from the sterilizer and the inner containers containing the enzyme substrate and nutrient medium were crushed. The indicators were then incubated at 60° C. and examined for fluorescence every hour for 5 hours using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation.

The number of growth positive indicators detected after 168 hours of incubation is recorded in Table 9. The percentages of these growth positive indicators that demonstrated fluorescence at 1 hr, 2 hr, 3 hr, 4 hr and 5 hr are also recorded in Table 9. For purposes of judging the accuracy of the sterilization indicators in Table 9, a fluorescence positive percentage of 100% is perfect, indicating that all growth positives were detected. A fluorescent positive number of less than 100%, on the other hand, indicates that there were one or more false negatives, in that some of the indicators that were negative for fluorescence were later detected as positive for spore growth.

The data in Table 9 indicates that the accuracy of sterilization indicators is improved in hydrogen peroxide plasma sterilization procedures, 2–3 hours after exposure, compared to indicators made with untreated spores, when the indicators are prepared with spores that have been treated with decaglyceryl decaoleate at concentrations of 5–100 mg/ml Decaglyceryl decaoleate was obtained from Lonza, Inc., Fairlawn, N.J.

TABLE 9

| COATING CHEMICAL | CONCENTRATION mg/ml | TOTAL TESTED[12] | NO. GROWTH POSITIVE 168 HR. | FLUORESCENCE - PERCENT POSITIVE 1 HR. | 2 HR. | 3 HR. | 4 HR. | 5 HR. |
|---|---|---|---|---|---|---|---|---|
| Untreated Control | — | 110 | 75 | 73.3 | 84.0 | 94.7 | 100 | 100 |
| Decaglyceryl Decaoleate | 5 | 65 | 35 | 65.7 | 100 | 100 | 100 | 100 |
| Decaglyceryl Decaoleate | 7.5 | 52 | 35 | 83.5 | 100 | 100 | 100 | 100 |
| Decaglyceryl Decaoleate | 10 | 100 | 49 | 83.7 | 100 | 100 | 100 | 100 |
| Decaglyceryl Decaoleate | 50 | 32 | 21 | 85.0 | 90.2 | 100 | 100 | 100 |
| Decaglyceryl Decaoleate | 100 | 38 | 30 | 73.3 | 86.7 | 100 | 100 | 100 |

[12]Total Tested = Total number of indicators exposed to the sterilization procedure.

Example 10

This Example reports the results of an experiment to determine whether the lumen-challenge test pack of the invention increases the resistance of a sterilization indicator within the test pack to a hydrogen peroxide plasma sterilization procedure.

Lumen-challenge test packs made according to the invention were exposed to partial and full cycles of a hydrogen peroxide plasma procedure, along with non-challenge test packs made according to the invention, a laboratory lumen-challenge device, and a sterilization indicator exposed without a test pack. The lumen-challenge test packs and the non-challenge test packs used in the Example included a sterilization indicator prepared as described above, with spores that had been treated with decaglycerol decaoleate at 5 mg/ml. The experimental lumen-challenge device included a carrier strip that was identical to the carrier strip in the sterilization indicators used in the test packs. The results of the experiment are reported in Table 10.

Four types of lumen-challenge test packs were prepared having lumen paths with lengths of 12 inches (30.48 cm), 9 inches (22.86 cm), 6 inches (15.24 cm) and 3 inches (7.62 cm), respectively. Each test pack had a lumen with a cross-sectional area equivalent to the area of a circle having a diameter of 0.25 inches (0.635 cm). The test packs included a test pack tray, a sterilization indicator and a lid.

The test pack trays were made by molding polyethylene terephthalate with a glycol additive (PETG), obtained from Eastman Kodak, Rochester, N.Y., in a Sencorp Model 1600 machine, obtained from Sencorp, Inc., Hyannis, Mass., using a pressure-forming process driven by vacuum and heat. The molds used in making the trays were made in a Fadal cutter machine, available from Fadal Engineering, a subsidiary of Gidding & Lewis, Inc., Chatsworth, Calif. The test pack trays were rectangular in shape and had a substantially planar surface. A recessed groove in the tray extended along a U-shaped path on the tray surface and penetrated the edge of the tray in two places, forming two lumen path openings through which sterilant could enter and leave the test pack during a sterilization procedure. The distance between the lumen path openings was 3.398 inches (8.630 cm). A semi-cylindrical trough having a radius of 0.219 inches (0.55626 cm) and a length of 2.435 inches (6.191 cm) was recessed into the tray at the midpoint of the lumen path, for holding a sterilization indicator in place during the sterilization procedure. The length of the side of the tray that included the lumen path openings, and of the side facing that side, was 4.300 inches (10.922 cm). The length of the other side varied depending on the length of the lumen path, and was 5.700 inches (14.478 cm) for the 12 inch (30.48 cm) lumen path test pack, 4.313 inches (10.955 cm) for the 9 inch (22.86 cm) lumen path test pack, 3.063 inches (7.780 cm) for the 6 inch (15.24 cm) lumen path test pack, and 1.938 inches (4.922 cm) for the 3 inch (7.62 cm) lumen path test pack. A sterilization indicator was placed in the trough of the test pack tray, and the tray was covered with a lid of SCOTCH-PAK™ polyester film, 0.85 mils thick, No. 29312, obtained from 3M Company, St. Paul, Minn. The film was heat-sealed to the tray using an ordinary clothes iron.

The non-challenge test pack included a test pack tray, a sterilization indicator and a lid. The test pack tray was made of PETG using the same molding process and machinery used to make the lumen-challenge test pack trays. The tray was rectangular in shape and had two sides with a length of 2.50 inches (6.35 cm) and two sides with a length of 4.20 inches (10.668 cm). An elevated rim with a flat top surface extended 0.50 inches (1.27 cm) inward from each side of the tray. A semi-cylindrical trough having a radius of 0.219 inches (0.55626 cm) and a length of 2.435 inches (6.191 cm) was recessed into the center of the tray for holding a sterilization indicator in place during a sterilization procedure. Grooves having a diameter of 0.25 inches (0.635 cm) were recessed into the elevated rim at each corner and at the midpoint of each side. The grooves extended completely through the elevated rim and formed a channel to carry sterilant to the sterilization indicator in the recessed trough during a sterilization procedure. A sterilization indicator was placed in the trough of the tray, and the tray was covered with a lid of SCOTCHPAK™ polyester film, 0.85 mils thick, No. 29312, obtained from 3M Company, St. Paul, Minn. The film was heat-sealed to the tray using an ordinary clothes iron.

The laboratory lumen-challenge device used in the Example was 30 cm long and included a stainless steel center section that was 5 cm long and had an internal diameter of 1.2 cm, and two stainless steel end sections that were each 10 cm long and had internal diameters of 4 mm. The ends of the center section were threaded and connected to fluted adapters, 2.5 cm long, which were attached to the end sections with rubber tubing. A carrier strip with treated spores was placed within the center section.

One set of devices was placed in an instrument tray and exposed to a full cycle of a hydrogen peroxide plasma sterilization procedure at 45–55° C. in a STERRAD™ 100SI GMP Sterilizer, obtained from Advanced Sterilization Products Co., Irvine, Calif. During the sterilization procedure a vacuum was drawn in the sterilization chamber for 5–6 minutes until the pressure was reduced to 300 mTorr. A 1.8 ml aliquot of an aqueous solution of 58–60% hydrogen peroxide was then injected into the sterilization chamber over a period of about 6 minutes, yielding an empty chamber concentration of 6–7 mg/ml hydrogen peroxide, and hydrogen peroxide vapor was allowed to diffuse throughout the chamber for 44 minutes at 6–10 Torr. A vacuum was then drawn, reducing the pressure to 500 mTorr and removing all detectable hydrogen peroxide vapor from the chamber. A plasma phase was then generated in the chamber by emitting an RF power source at 400 watts and 13.56 MHz for about 15–16 minutes at 500 mTorr, after which the chamber was vented for 3–4 minutes until atmospheric pressure was reached in the chamber.

A second set of devices was placed in an instrument tray and exposed to a partial cycle of a hydrogen peroxide plasma sterilization procedure at 45–55° C. in the STERRAD™ 100SI GMP Sterilizer. In the partial cycle, hydrogen peroxide vapor was allowed to diffuse throughout the chamber for only 9 minutes, as compared to the much longer period of diffusion in the full cycle. Otherwise the partial cycle and the full cycle were the same.

After exposure to the sterilization procedure the test packs, sterilization indicators and laboratory lumen challenge devices were removed from the sterilizer, and the sterilization indicators were removed from the test packs. The carrier strip was aseptically removed from the experimental lumen challenge device and combined with the other components necessary to make a sterilization indicator, as described above, identical to the sterilization indicators used in the test packs. The inner containers of the sterilization indicators containing the enzyme substrate and nutrient medium were then crushed. The indicators were then incubated at 60° C. and examined for fluorescence after 5 hours using a 3M™ ATTEST™ Model 190 Rapid Autoreader, commercially available from 3M Company, St. Paul, Minn. Additionally, spore growth, as indicated by a color change from purple to yellow, was determined visually after 168 hours of incubation.

The number of growth positive indicators detected after 168 hours of incubation is recorded in Table 10. The number of fluorescent positives detected after 5 hours is also recorded in Table 10.

The fractional cycle data in Table 10 indicates that the six inch, nine inch and twelve inch lumen-challenge test packs of the invention provide a challenge to hydrogen peroxide plasma sterilization procedures that is greater than the challenge provided by sterilization indicators exposed without the test packs, and that the non-challenge test pack of the invention provides a challenge that is equivalent to that of a sterilization indicator exposed without a test pack.

TABLE 10

| DEVICE | FRACTIONAL CYCLE | | | FULL CYCLE | | |
|---|---|---|---|---|---|---|
| | TOTAL EXPOSED | FLUORESCENCE –5 HOURS | GROWTH READOUT –7 DAYS | TOTAL EXPOSED | FLUORESCENCE –5 HOURS | GROWTH READOUT –7 DAYS |
| 12 in. lumen test pack | 1 | 1 | 1 | 1 | 0 | 0 |
| 9 in. lumen test pack | 1 | 1 | 1 | 1 | 0 | 0 |
| 6 in. lumen test pack | 1 | 1 | 1 | 1 | 0 | 0 |
| 3 in. lumen test pack | 1 | 0 | 0 | 1 | 0 | 0 |
| Sterilization indicator | 1 | 0 | 0 | 1 | 0 | 0 |
| Laboratory lumen challenge device | 1 | 1 | 1 | 1 | 0 | 0 |
| Non-challenge test pack | 1 | 0 | 0 | 1 | 0 | 0 |

What is claimed is:

1. A sterilization indicator for testing the effectiveness of a sterilization procedure, comprising:

(a) a compressible outer container having at least one opening to allow sterilant to enter the outer container during the sterilization procedure;

(b) a source of an active enzyme contained within the outer container, the enzyme having an enzyme activity that is correlated with the survival of at least one test microorganism commonly used to monitor the effectiveness of a sterilization procedure, wherein the enzyme is substantially inactivated by a sterilization procedure that is lethal to the test microorganism, but wherein the enzyme may not be substantially inactivated by a sterilization procedure that is sublethal to the test microorganism;

(c) a sterilant-resistant chemical associated with the source of active enzyme in such a manner that the active enzyme is more resistant to inactivation by a sterilization procedure than it would be if it were not associated with the sterilant-resistant chemical; and (d) a breakable inner container within the outer container that is impermeable to the sterilant used in the sterilization procedure and that contains a substrate, wherein the inner container is adapted so that it may be broken by compressing the outer container, to allow the substrate to react with active enzyme to form an enzyme-modified product that provides a detectable indication of the failure of a sterilization procedure.

2. A sterilization indicator according to claim 1, wherein the source of an active enzyme comprises a microorganism.

3. A sterilization indicator according to claim 2, wherein the source of an active enzyme comprises *Bacillus stearothermophilus* spores.

4. A sterilization indicator according to claim 1, wherein the source of an active enzyme comprises a purified enzyme.

5. A sterilization indicator according to claim 1, wherein the sterilant-resistant chemical comprises a surfactant.

6. A sterilization indicator according to claim 5, wherein the sterilant-resistant chemical further comprises a surfactant and a hydrophobic additive.

7. A sterilization indicator according to claim 1, wherein the sterilant-resistant chemical comprises a polyglycerol alkyl ester or a polyglycerol alkyl ether.

8. A sterilization indicator according to claim 7, wherein the sterilant-resistant chemical is a compound selected from the group consisting of decaglyceryl monostearate, hexaglyceryl monostearate, tetraglyceryl monostearate, hexaglyceryl polyricinolate, decaglyceryl monolaurate, hexaglyceryl monolaurate, tetraglyceryl monolaurate, decaglyceryl trioleate, decaglyceryl monooleate, decaglyceryl dipalmitate, hexaglyceryl distearate, decaglyceryl monooleate, decaglyceryl monomyristate, decaglyceryl monoisostearate, and decaglyceryl diisostearate, and mixtures of two or more members of the group.

9. A sterilization indicator according to claim 1, wherein the sterilant-resistant chemical comprises an ethoxylated polyhydric alcohol ester or an ethoxylated polyhydric alcohol ether.

10. A sterilization indicator according to claim 9, wherein the sterilant-resistant chemical is a compound selected from the group consisting of glycereth-7-diisononanoate, polyoxyethylene (5) glyceryl monostearate, and mixtures of two or members of the group.

11. A sterilization indicator according to claim 1, wherein the sterilant-resistant chemical comprises decaglycerol.

* * * * *

UNITED STATES PATENT AND TRADEMARK OFFICE
CERTIFICATE OF CORRECTION

PATENT NO. : 6,897,059 B2
DATED : May 24, 2005
INVENTOR(S) : Foltz, William E.

It is certified that error appears in the above-identified patent and that said Letters Patent is hereby corrected as shown below:

Title page,
Item [56], References Cited, U.S. PATENT DOCUMENTS, after
"Antonoplos et al" insert -- . --;
OTHER PUBLICATIONS,
"Kokufuta" reference, delete "Useful" and insert in place thereof -- Use --;
"Laurence" reference, delete "in" and insert in place thereof -- on --;
"Torchilin" reference, after "Annals" delete the word "of";
"Udenfriend" reference, delete "Fluorecence" and insert in place therefor
-- Fluorescence --;

Column 9,
Line 60, delete "dmethicones" and insert in place thereof -- dimethicones --;

Column 32,
Line 18, delete "3m$^{TM}$" and insert in place thereof -- 3M$^{TM}$ --;

Column 38,
Line 47, after "or" insert -- more --.

Signed and Sealed this

Sixth Day of December, 2005

JON W. DUDAS
*Director of the United States Patent and Trademark Office*